US011046952B2

(12) United States Patent
Blainey et al.

(10) Patent No.: US 11,046,952 B2
(45) Date of Patent: Jun. 29, 2021

(54) ENCODING OF DNA VECTOR IDENTITY VIA ITERATIVE HYBRIDIZATION DETECTION OF A BARCODE TRANSCRIPT

(71) Applicants: THE BROAD INSTITUTE, INC., Cambridge, MA (US); MASSACHUSETTS INSTITUTE OF TECHNOLOGY, Cambridge, MA (US)

(72) Inventors: Paul Blainey, Cambridge, MA (US); David Feldman, Redmond, WA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 130 days.

(21) Appl. No.: 15/558,504

(22) PCT Filed: Mar. 16, 2016

(86) PCT No.: PCT/US2016/022718
§ 371 (c)(1),
(2) Date: Sep. 14, 2017

(87) PCT Pub. No.: WO2016/149422
PCT Pub. Date: Sep. 22, 2016

(65) Prior Publication Data
US 2018/0080019 A1 Mar. 22, 2018

Related U.S. Application Data

(60) Provisional application No. 62/133,821, filed on Mar. 16, 2015, provisional application No. 62/133,539, filed on Mar. 16, 2015.

(51) Int. Cl.
*C12N 15/10* (2006.01)
*C12N 15/63* (2006.01)

(52) U.S. Cl.
CPC ....... *C12N 15/1065* (2013.01); *C12N 15/102* (2013.01); *C12N 15/1079* (2013.01); *C12N 15/1082* (2013.01); *C12N 15/63* (2013.01)

(58) Field of Classification Search
CPC .... C12N 15/1065; C12N 15/63; C12N 15/85; C12N 15/86; C12N 15/80–82; C12N 15/1082; C12N 2310/20; C12N 15/8213; C12N 15/902–15/907; C12N 15/64; C12N 15/65; C12N 15/66; C12N 15/67; C07K 2319/95
See application file for complete search history.

(56) References Cited

U.S. PATENT DOCUMENTS

| | | | |
|---|---|---|---|
| 2004/0146987 A1* | 7/2004 | Zdanovsky | C12N 15/67 435/69.7 |
| 2005/0026286 A1 | 2/2005 | Chi et al. | |
| 2009/0098555 A1* | 4/2009 | Roth | C12Q 1/6816 435/6.12 |
| 2009/0203148 A1 | 8/2009 | Gorfinkel et al. | |
| 2011/0021369 A1* | 1/2011 | Mhlanga | C12Q 1/6897 506/9 |
| 2014/0031243 A1 | 1/2014 | Cai et al. | |
| 2014/0068797 A1* | 3/2014 | Doudna | A01K 67/027 800/18 |
| 2014/0186958 A1* | 7/2014 | Zhang | C12N 9/22 435/462 |
| 2014/0227701 A1 | 8/2014 | Samson et al. | |
| 2015/0071906 A1* | 3/2015 | Liu | A61K 38/465 424/94.6 |
| 2015/0191744 A1* | 7/2015 | Wolfe | C12N 15/86 435/6.11 |
| 2018/0051319 A1* | 2/2018 | Rotem | C12Q 1/68 |

FOREIGN PATENT DOCUMENTS

| | | | | |
|---|---|---|---|---|
| WO | WO-0214553 A2 * | 2/2002 | | C12N 15/10 |
| WO | 2014030066 A2 | 2/2014 | | |
| WO | WO-2014093701 A1 * | 6/2014 | | C12N 15/63 |
| WO | WO-2014099744 A1 * | 6/2014 | | C12N 15/87 |
| WO | WO-2015095501 A1 * | 6/2015 | | C40B 20/04 |

(Continued)

OTHER PUBLICATIONS

Entry for "catalysis" in Miller-Keane Encyclopedia and Dictionary of Medicine, Nursing, and Allied Health, Seventh Edition. 2003 by Saunders, an imprint of Elsevier, Inc., printed as p. 1/1. (Year: 2003).*
Miyagawa et al. Identification of cis- and trans-acting factors involved in the localization of MALAT-1 noncoding RNA to nuclear speckles. RNA, vol. 18, pp. 738-751,2012. (Year: 2012).*
Eliscovich et al. mRNA on the move: The road to its biological destiny. Journal of Biological Chemistry, vol. 288, No. 28, p. 20361-20368, Jul. 2013, in press May 2013. (Year: 2013).*
Weiss et al. Protein targeting to subcellular organelles via mRNA localization. Biochimica et Biophysica Acta, vol. 1833, pp. 260-273, 2013, available online Apr. 2012. (Year: 2012).*

(Continued)

*Primary Examiner* — Jennifer Dunston
(74) *Attorney, Agent, or Firm* — Johnson, Marcou, Isaacs & Nix, LLC; F. Brent Nix, Esq.; Rachel D. Rutledge, Esq.

(57) ABSTRACT

Embodiments disclosed herein are directed to a new genetic perturbation and screening method that combines advantages of pooled perturbation with imaging assays for complex phenotypes. Specifically, the method may be used to screen pooled genomic perturbations to identify phenotypes and to identify perturbed genes at the single-cell level using optical barcodes. A major advantage offered by this approach is the ability to screen for any cellular phenotype that can be identified by high-resolution microscopy—including live-cell phenotypes, protein localization, or highly multiplexed expression profile and mRNA localization by RNA-FISH—in conjunction with a large array of genetic perturbations applied as a pool in a single test volume.

32 Claims, 16 Drawing Sheets

(56) References Cited

FOREIGN PATENT DOCUMENTS

WO    2016007063 A1    1/2016

OTHER PUBLICATIONS

Jambhekaretal. RNA, vol. 13, pp. 625-642, 2007. (Year: 2007).*
Singer-Kruger et al. Here, there, everywhere. RNA Biology, vol. 11, No. 8, pp. 1031-1039, Aug. 2014. (Year: 2014).*
Wijshake et al. Endonucleases: new tools to edit the mouse genome. Biochimica Biophysica Acta, vol. 1842, pp. 1942-1950, Apr. 30, 2014. (Year: 2014).*
Lee et al. Designed nucleases for targeted genome editing. Plant Biotechnology Journal, vol. 14, pp. 448-462, 2016, EPub Sep. 15, 2015. (Year: 2015).*
Guilinger et al. Fusion of catalytically inactive Cas9 to FokI nuclease improves the specificity of genome modification. Nature Biotechnology, vol. 32, No. 6, pp. 577-582, Apr. 25, 2014, including p. 1/1 of Online Methods. (Year: 2014).*
Lee et al. Fluorescent in situ sequencing (FISSEQ) of RNA for gene expression profiling in intact cells and tissues. Nature Protocols, vol. 10, No. 3, pp. 442-458, Feb. 12, 2015, including p. 1/6-6/6 of Supplementary Information. (Year: 2015).*
Ng et al. Application of destabilizing sequences on selection marker for improved recombinant protein productivity in CHO-DG44. Metabolic Engineering, vol. 9, pp. 304-316, 2007. (Year: 2007).*
Punetha et al. Short read (next-generation) sequencing. Circulation. Cardiovascular Genetics, vol. 6, No. 4, pp. 427-434, Aug. 2013. (Year: 2013).*
Metzker, ML. Sequencing technologies—the next generation. Nature Reviews Genetics, vol. 11, pp. 31-46, Jan. 2010, published online Dec. 8, 2009. (Year: 2009).*
Bandaranayake et al. Recent advances in mammalian protein production. FEBS Letters, vol. 588, pp. 253-260, 2014, available online Dec. 6, 2013. (Year: 2013).*
Hwang et al. When a ribosome encounters a premature termination codon. BMB Reports, vol. 46, No. 1, pp. 9-16, 2013. (Year: 2013).*
Batish, et al., "Batish M, et al. Single molecule imaging of RNA in situ. Methods Mol Bio 714:3-13, 2011."
Carpenter, "Carpenter AE, Jones TR, Lamprecht MR, Clarke C, Kang IH, Friman O, Guertin DA, Chang JH, Lindquist RA, Moffat J, Golland P, Sabatini DM. CellProfiler: image analysis software for identifying and quantifying cell Phenotypes. Genome Biology 7:R100, 2006."
Hiatt, et al., "Parallel, Tag-directed Assembly of Locally Derived Short Sequence Reads", Nature Methods, vol. 7, No. 2, Feb. 2010, p. 119 XP055005905, Jan. 17, 2010, 1-7.
Ke, et al., "In situ sequencing for RNA analysis in preserved tissue and cells." Nature methods 10.9 (2013): 857, 6 pages.
King, "King IF, et al. Topoisomerases facilitate transcription of long genes linked to autism. Nature 501(7465):58-62, 2013."
Larson, et al., "CRISPR Interference (Crispri) for Sequence-Specific Control of Gene ExpressionCRISPR Interference (Crispri) for Sequence-Specific Control of Gene Expression", Nature Protocols, vol. 8, No. 11, 2013, 2180-2196.
Nieland, et al., "High Content Image Analysis Identifies Novel Regulators of Synaptogenesis in a High-Throughput RNAi Screen of Primary Neurons. PLoS One, 9(3): e91744, 2014".
O'Roak, et al., "Multiplex Targeted Sequencing Identifies Recurrently Mutated Genes in Autism Spectrum Disorders", Science, vol. 338, No. 6114, Dec. 21, 2012, 1619-1622.
Sanjana, et al., "A Transcription Activator-like Effector Toolbox for Genome Engineering", Nature Protocol, vol. 7, Issue 1, Jan. 2012, 171-192.
Sanjana, et al., "Improved Vectors and Genome-Wide Libraries for CRISPR Screening", Nature Methods, vol. 11, No. 8, Aug. 2014, 783-784.
Shalem, et al., "Genome-Scale CRISPR-Cas9 Knockout Screening in Human Cells", Science, vol. 343, No. 6166, Jan. 3, 2014, 84-87.
"PCT International Preliminaryl Report on Patentability", dated Sep. 19, 2017, 1-9.
International Search Report and Written Opinion for PCT International Application No. PCT/US2016/022718, dated Jun. 10, 2016, 17 pages.

* cited by examiner

ENCODING OF DNA VECTOR IDENTITY VIA ITERATIVE HYBRIDIZATION DETECTION OF A BARCODE TRANSCRIPT

CROSS-REFERENCE TO RELATED APPLICATIONS

The present application is a 35 U.S.C. § 371 national stage application of International Patent Application No. PCT/US2016/022718 filed on Mar. 16, 2016, which claims the benefit of U.S. Provisional Patent Application No. 62/133,821 filed Mar. 16, 2015 and U.S. Provisional Patent Application No. 62/133,539 filed Mar. 16, 2015. The entire contents of the above-referenced applications are hereby incorporated in their entirety herein.

TECHNICAL FIELD

The subject matter disclosed herein is directed to methods and materials for genome-wide screening of genetic perturbations combined with imaging assays for complex phenotypes to identify relationships between genotypes and phenotypes.

BACKGROUND

Identifying gene function and impact on disease biology are overarching aims of life science research in the post-genomic era and underpin efforts to understand the meaning of genetic variation in human populations. However, crucial gaps remain in the functional genomics tool set that will slow our progress in using genomics to unravel disease biology. Currently, efficient pooled methods for genome-wide screening require either selection of cells based on growth advantage, or physical purification, e.g. by whole-cell fluorescence (using FACS). Many disease processes are characterized by more complex cellular phenotypes including defects in cell or organelle morphology, subcellular localization, cell motility, or gene expression signatures. Other phenotypes of interest may involve transient states (e.g., mitosis), cell-cell interaction, or require dynamic, optical assays (e.g., optogenetic recording of neuronal activity). Image-based, high-content screens using cDNA and RNA interference have uncovered novel genes involved in complex phenotypes, including mitosis, synaptogenesis, and embryogenesis. However, such microplate-based screens are not regularly conducted at the genomic scale due to the expense, labor and automation expertise required. Although "living cell array" screens have reduced some logistical hurdles[1], they still require individually synthesizing and arraying each gene perturbation reagent.

SUMMARY

A method for screening cells for genetic modification comprises culturing a cell or cell population in one or more discrete volumes. One or more vectors, such as a viral vector, are delivered into the individual cell or population of cells in each discrete volume. The vectors comprise nucleic acid sequences that encode one or more optical barcodes and one or more genetic perturbations. Each genetic perturbation to be introduced is assigned a unique optical barcode. In some embodiments, a specific combination of genetic perturbations, such as a combination of perturbations encode in the same vector, may be assigned a single optical barcode. The optical barcode comprises an ordered series of segments. For each segment there are a set of possible nucleic acid sequences that can be found at that segment. Each of the possible nucleic acid sequences at a segment comprise a unique sequence and are designed to bind to a corresponding probe. Each probe is labeled with a different optically detectable label. The cells are incubated to allow for expression of a mRNA transcript comprising the optical barcode. The sequence of the optical barcode is then detected. This may be achieved, for example, by the sequential hybridization, imaging, washing, and re-imaging of probe sets designed to bind each of the possible unique nucleic acid sequences found at each segment of the optical barcode. That is each optical barcode encodes the order in which certain labeled probes should bind to the optical barcode over multiple rounds of binding and imaging of probe sets. Detection of this observed order of labeled probes can therefore be used to identify the optical barcode which in turn identifies the type of genetic perturbation(s) delivered to a particular cell or cell population. In addition to imaging to detect the optical barcode, each discrete volume may be imaged to determine an observed phenotype for each cell or cell population. The observed phenotype in each discrete volume may then be correlated back to the corresponding genetic perturbation(s) introduced into each particular cell or cell population.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

FIG. 3A Cells infected with the barcoded virus pool are marked by GFP and mixed to attain desired ratio of wild-type to modified cells. The morphology of each perturbed cell is then assessed by high content imaging at the scale of >1000 cells per unique pair of perturbations (numbers given for 100×100 screen). FIG. 3B After fixation, cells are subjected to sequential RNA-FISH staining and imaging. At each round of FISH, one of four sequences marked by color is detected on each of the two barcodes present. By deduction, only a single pair of perturbations can produce the observed sequence of FISH images, allowing unambiguous identification of the perturbations received by the cell.

FIG. 5A Barcodes are designed by assembling 20-mer probes filtered for GC content, secondary structure, cross-hybridization, and off-target binding to transcriptome of target cells. FIG. 5B Each target sequence is synthesized once, then recombined to generate all barcodes. For small libraries, barcodes are inserted into a lentiviral backbone and sequence-verified from a plate of colonies. Large libraries are characterized using NGS. A single set of barcoded plasmids can be used with any sgRNAs. FIG. 5C Construct architecture that ensures only selected cells express barcode. FIG. 5D Barcode detection assessment. Variance in barcode expression, barcoding error rate, and optical phenotyping are benchmarked in a single experiment using known control genotypes.

FIG. 6A) Repeated three rounds of FISH (Round 1, 2 and 3 shown) identify the sgRNA present in each cell. Data shown is for probes targeting endogenous GAPDH and GFP transcripts. Exposure time, excitation power, and display contrast are identical in all images (scale bar: 15 μm). FIG. 6B) Fluorescent probes retain high specificity after multiple rounds of FISH (left panel). Mean FISH signal and background calculated for data in (6A) (right panel) (grey bar: +/−2 std). FIG. 6C) Barcoding capacity scales geometrically with number of FISH rounds. Dual-labeled probes (e.g., green+red) allow 10-plex FISH on a standard 4 color microscope.

DETAILED DESCRIPTION OF THE EXAMPLE EMBODIMENTS

Figures 1A, 1B, 1C, 1D, 1E:
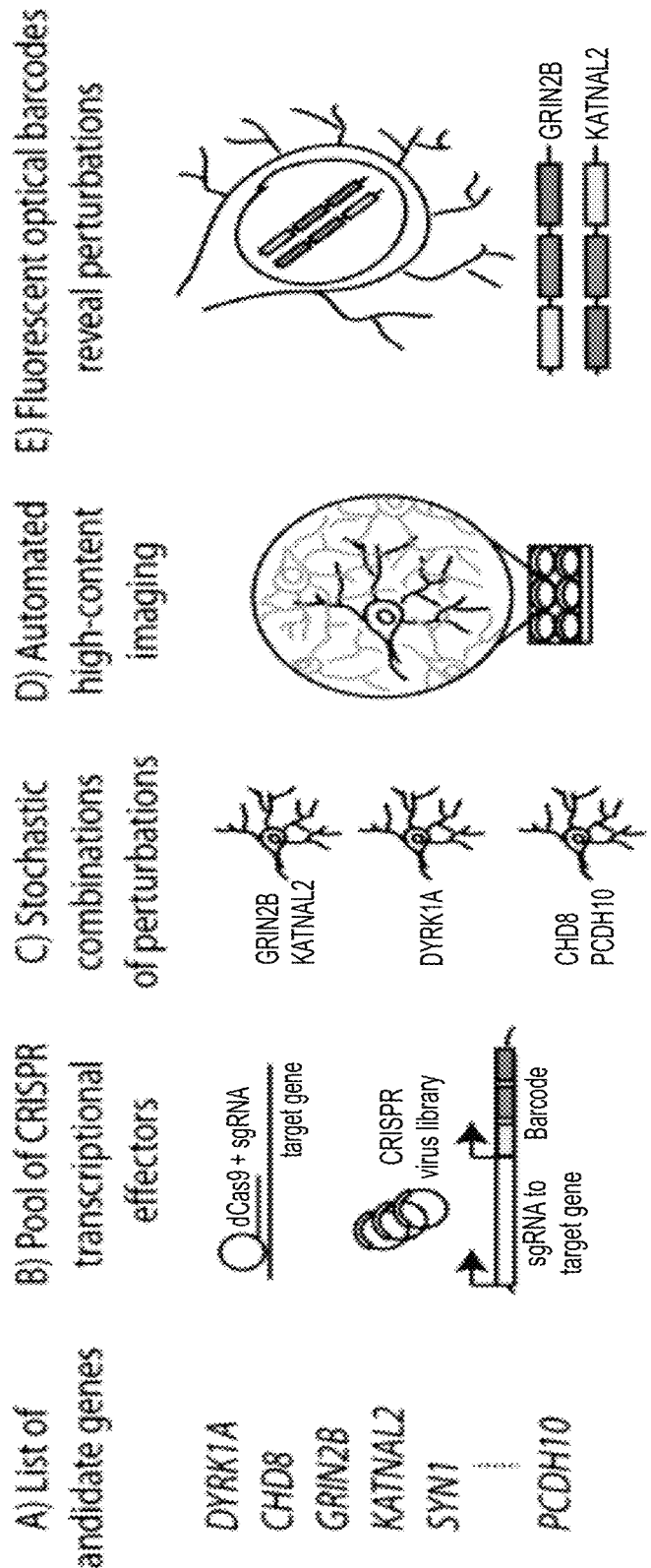
FIG. 1A-1E is a schematic showing an overview of the process described herein, in accordance with certain example embodiments. Individual cells receive a combination of random perturbations from a virus library delivering CRISPR transcriptional effectors. Cells are then cultured together under uniform conditions and phenotyped at the single-cell layer, including the morphology of the cell with wild type background cells. An optical barcoding and imaging scheme allows exact recovery of the perturbations received by each cell to measure the relationship between pairs of variants.

Embodiments disclosed herein are directed to a new genetic perturbation and screening method that combines advantages of pooled perturbation with imaging assays for complex phenotypes. Specifically, the method may be used to screen pooled genomic perturbations to identify phenotypes and to identify perturbed genes at the single-cell level. A major advantage offered by this approach is the ability to screen for any cellular phenotype that can be identified by high-resolution microscopy—including live-cell phenotypes, protein localization, or highly multiplexed expression profile and mRNA localization by RNA-FISH—in conjunction with a large array of genetic perturbations applied as a pool in a single test volume. This combines the principal benefits of today's pooled (low cost) and arrayed (high information content) screens with single-cell resolution. The embodiments disclosed herein provide in situ approaches based on serial probing with labeled oligonucleotides, and are highly suited to screening in cultured and primary cells, post-mitotic cells, such as neural cells, and tissue sections. The methods disclosed herein can be applied to combinatorial screens where two or more genetic perturbations per cell need to be assessed.

A pooled library of transcriptional effectors for introducing one or more genetic perturbations is designed and cloned into a suitable vector. For example, the library may contain a set of plasmids or other suitable delivery vectors with each delivery vector encoding one or more genetic perturbations. The genetic perturbations may include a gene knock-in, a gene-knock out, or one or more nucleotide insertions deletions, substitutions, or mutations. The genetic perturbation may be generated using, for example, CRISPR/Cas9, RNAi (siRNA and shRNA), TALEN, Zn Finger enzymes, site directed mutagenesis, or other genetic engineering methods known in the art, or a combination thereof.

In certain example embodiments, the vectors encode one or more optical barcodes. In certain example embodiments, each vector encodes a single optical barcode per vector. An optical barcode comprises an ordered combination of segments. Each segment is designed to be recognized by a probe, or sub-set of probes, having a particular type of optically detectable label. Thus, for a first segment there will be a number of unique sequences equal to the number of probes that will be used in the method. For example, if four different optically detectable labels are being used, then at the first segment there will be four unique sequences each capable of hybridizing to only one of the four different probes labeled with one of the four different detectable labels. Likewise, at the second segment there are four unique sequences each individual sequence binding a different probe with a different one of the four detectable labels being used and so on for each segment in the optical barcode. In certain example embodiments, there are multiple copies of each unique nucleic acid sequence to allow for multiple corresponding probes to bind to a segment in order to enhance the detectable signal.

In certain example embodiments, the optical barcode comprises 2, 3, 4, 5, 6, 7, 8, 9, or 10 segments (ordered positions). Each segment may comprise 20 to 250 base pairs. The size of each segment will depend, at least in part, on the number of probes to be bound to each segment. Design factors dictating the size of each segment include the number of probes to be bound to each segment, remaining within a base pair size range that can be read by a desired sequencing method and remaining within the general size realm of natively expressed mRNA transcripts. In one example embodiment, each segment is approximately 200 bp each targeted with 8, 20 bp probes. The resulting barcode is 1-1.5 kb, remaining within the limits of Sanger sequencing and mRNA transcripts. The sequences of the barcode segments and matching probes are designed to minimize off-target binding to the transcriptome, binding between probes (crosstalk), and secondary structure. Once optimal sequences for each segment are identified, all random combinations of the segments may be cloned. For example, each unique nucleic acid sequence binding a particular labeled probe for each segment can be synthesized and then digested and randomly ligated into the various combinations that will define each optical barcode using methods known in the art. See FIG. 5A-5D.

Thus, expression of the vector will result in expression of a RNA transcript comprising the optical barcode. The optical barcodes may be constitutively expressed or may be under the control of an inducible promoter. In certain example embodiments, the optical barcode is under the control of a CMV promoter. In certain example embodiments, the nucleic acid encoding the optical barcode may further comprise a premature termination signal to prevent translation of the RNA transcript comprising the optical barcode. In certain example embodiments, the optical barcode may further comprise a localization signal to localize the expressed RNA transcript comprising the optical barcode to a particular cellular location. Cellular localization signals are known in the art and can be selected based on a desired target location for localizing the transcript in the cell. In certain example embodiments, the localization signal is a cellular nucleus localization sequence. In one example embodiment, the nuclear localization signal is a 3' UTR stem loop, including stem loops from viral transcripts and the lncRNA MALAT1. In certain example embodiments, the optical barcode may further comprise a unique molecular identifier (UMI). The UMI is a short nucleotide sequence that can be used as an identifier for a specific optical barcode. For example, use of a UMI can allow sequencing of just the UMI to identify the optical barcode encoded in a given vector.

In certain example embodiments, the vector may further encode an antibiotic resistance gene. The antibiotic resistance gene may be under control of the same promoter as the optical barcode. Different levels of expression of the optical barcode may be observed between vectors or different cells. Minimal expression may be assured by antibiotic selection. Further, selection for higher expressing constructs or cells may be desirable to increase the detectable signal of optical barcodes. Selection for higher level baseline expression may be selected if the antibiotic resistance protein is rapidly degraded. Accordingly, in certain example embodiments, the vectors may further encode fusion of a short degradation domain to the N- or C-terminus of the antibiotic resistance gene. Example degradation domains include FKBP degradation domains and DHFR degradation domains. Furthermore, the degradation rate is tunable using cell-permeable small-molecule ligands known in the art. See Björklund et al. "A General Chemical Method to Regulate Protein Stability in the Mammalian Central Nervous System. Chemistry & Biology" Chemistry & Biology 2010, 17(9):981-88. Thus, the methods disclosed herein may further comprise a selecting step, wherein the selecting step comprises exposing cells expressing the one or more vectors described herein to an antibiotic and selecting those cells that maintain optical barcode expression levels above a desired cut-off in the presence of the antibiotic.

A vector encoding a unique optical barcode may be delivered to a discrete volume receiving one of the above described genetic perturbations. The vector may be delivered to a discrete volume receiving the genetic perturbation prior to, concurrently with, or after the genetic perturbation is introduced. The term discrete volume is defined further below.

In certain example embodiments, the vectors further encode a site specific nuclease capable of introducing the genetic perturbation into a target sequence within a cell or population of cells. Site specific nucleases include, but are not limited to, e.g., a zinc-finger nuclease (ZFN), a transcription activator-like effector nuclease (TALENs) and/or a CRISPR system comprising a dCas9 and sgRNA. In certain example embodiments, the site-specific nuclease is a dCas9 nuclease. In certain example embodiments, the dCas9 is fused to a second domain. In certain example embodiments, the second domain is a nickase, a transcriptional activator, a transcriptional repressor, a recombinase, a transposase, a DNA or histone methyltransferases, a histone nucleases, or an endonuclease recognizing chromatin remodeling loci, such as CTCF sites at loop anchors. In certain example embodiments, the dCas9 may be catalytically inactive, for example to repress target gene expression.

In certain example embodiments, the vectors encode a dCas9 nuclease, a short guide RNA (sgRNA) and the optical barcode. In certain example embodiments, the sgRNA and optical barcode may be under the control of the same promoter or a separate promoter. In certain example embodiments, optical barcodes may be matched to sgRNAs using a gateway vector. Compared to the final vectors described above, the gateway vector is modified so that the sgRNA and barcode lie adjacent to one another but separated by a cloning site. The intervening sequence is inserted after both the sgRNA and barcode are inserted into the gateway vector. The intervening sequence may comprise the 3' constant region of the sgRNA, the barcode promoter, and any sequence 5' to the barcode. This method allows short-read DNA sequencing (e.g. Illumina) of the sgRNA-barcode pair. Full length optical barcodes may range from 1-2kb. For efficient sequencing, the optical barcodes are first sequenced to match the full barcode to a unique identifier of 20 "N" bases at the 5' end of the barcode. All subsequent sequencing of this barcode pool requires sequencing just the 20 bp UMI and adjacent sequence of interest (e.g. sgRNA), rather than the full-length barcode. Similar "tag sequencing" methods are described in the literature. See J. B. Hiatt et al. Nature Methods 2010, 7(2):119-22.

Random cloning of sgRNAs to optical barcodes may inherently limit optical barcoding capacity and result in adequate representation of certain sgRNAs. Thus, in certain example embodiments, the sgRNAs may be synthesized with a barcode UMI-specific homology sequence, for example a 20 bp homology sequence, allowing one-to-one cloning of sgRNAs to optical barcodes. Suitable cloning methods include, for example, Gibson assembly, ligation-independent cloning, and ligation by molecular inversion probes.

In certain example embodiments, the vectors may further encode a detectable marker such as GFP to allow tracing of the whole cell body of cells successfully transfected with a vector.

Any suitable vector for delivering the constructs to a single cell or population of cells may be used. In certain example embodiments, the vector is a viral vector. In another example embodiments, the viral vector is a lentiviral vector.

Detection of Phenotype and Genotype Using Optical Barcodes

The above described constructs are introduced into a single cell or population of cells. The cells may be cultured cells, primary cells, post-mitotic cells, such as neural cells, and tissue sections. The cell or population of cells to be screened are cultured in separate discrete volumes. In certain example embodiments, a single discrete volume is used. As used herein, a "discrete volume" or "discrete space" may refer to a container, receptacle, or other defined volume or space that can be defined by properties that prevent and/or inhibit migration of molecules, particles and/or cells. For example, a discrete volume or space may be defined by physical properties such as walls of a discrete well, tube, or surface of a droplet which may be impermeable or semi-permeable. In certain example embodiments, the discrete volume may be any standard tissue culture container such as a tissue culture plate or flask. In certain example embodiments, the discrete volume may be the wells of a standard microwell plate, such as 6 well, 24 well, 96 well, 384 well, or 1,536 well plate. The microwell plate may be made of any material suitable for imaging of the discrete volumes using the imaging modalities described herein. In certain example embodiments, the discrete volume may be a culture chamber in an array of culture chambers defined on a microfluidic device, or droplet generated on a microfluidic device.

One or more genetic perturbations are introduced into the individual cells or cell populations in each discrete volume. As noted above, the genetic perturbation may be introduced prior to, concurrent with, or subsequent to delivery of the one or more vectors described above. A single optical barcode identifying the particular genetic perturbation introduced into each cell or cell population is delivered to each discrete volume. In certain example embodiments, the one or more vectors encode both the optical barcode and a site-specific nuclease for introducing the genetic perturbation into the cell or population of cells. Delivery of the one or more genetic perturbations and/or one or more vectors encoding the one or more optical barcodes may be achieved using standard delivery techniques known in the art.

The individual cells or cell populations are incubated for a time sufficient to allow expression of the RNA transcript encoding the optical barcode. The effect of the genetic perturbation may be assessed in the presence of different conditions or challenges to the cells such as, but not limited to, exposure of the individual cells or cell populations to therapeutic agents, or combinations of therapeutic agents at different concentrations and/or durations of exposure. The individual cell or population of cells may also be exposed to different physical parameters such as, but not limited to, different temperatures, atmospheric pressures, atmospheric $CO_2$ concentrations, atmospheric $O_2$ concentrations, changes in pH, changes to the composition of the culture media, such as introduction of different additives at varying concentrations and/or durations of exposure, or a combination of any of the above.

Optical assessment of each discrete volume may be made to determine a phenotype of the individual cells or cell population. Optical assessments may be recorded for later use. In one embodiment, observable cell phenotypes may include, but are not limited to, changes in morphology, motility, and cell death. Optical assessments may also include cell-cell contact such as, but not limited to, antigen presentation and synapsing, and interaction with a patterned substrate such as, but not limited to, patterned extracellular matrix proteins. In certain example embodiments, an additional imaging agent may be delivered to cells. For example, dyes or stains that label certain sub-cellular components such as the nucleus, cytoskeleton, endoplasmic reticulum, mitochondria, or cell wells. In addition, molecule-specific labeling agents such as labeled antibodies or labeled nucleic acids may be used to track changes in localization of certain target molecules. In one embodiment, acellular systems may be assessed using optical assays for protein:protein interactions, quantitation of components of interest, enzymatic activity, and the like.

The limiting factor in scale is the ability to image cells. It is estimated the method disclosed herein may analyze 10,000 perturbations replicated 1000-fold at the single-cell level, for a total of 10,000,000 single-cell assays in a screen, assuming use of a typically operated research microscope, such as the Opera Phenix (PerkinElmer), which can image up to $10^8$ cells per day. Accordingly, as the scale of imaging increases, the scale of the methods disclosed herein may increase as well.

Next, the expressed optical barcodes are detected. Because a unique optical barcode is assigned to each type of genetic perturbation, read-out of the optical barcode allows the observed phenotypes described above to be correlated to a particular genotype. Each discrete volume is imaged with the appropriate imaging technique to detect the optical barcode. For example, if the optical barcodes are detected using binding by fluorescently labeled probes, each discrete volume is imaged using a fluorescent microscope. In another example, if the optically encoded particles are colorimetrically labeled, each discrete volume is imaged using a microscope having one or more filters that match the wave length or absorption spectrum or emission spectrum inherent to each color label. Other detection methods are contemplated that match the optical system used, e.g., those known in the art for detecting quantum dots, dyes, etc.

In one example embodiment, the optical barcodes are detected by sequential delivery of probe sets to each individual discrete volume under conditions sufficient to allow binding by the probes of the probe set to a corresponding segment of the optical barcodes. Thus, for detecting the unique nucleic acid sequences possible at the first segment of an optical barcode, a first probe set comprising probes that recognize one of the unique nucleic acid sequences at the first segment are delivered to each discrete volume, with each probe that recognizes a different unique nucleic acid sequence being labeled with a different optically detectable label. In certain example embodiments, the probes are 20 mer probes. In certain example embodiments, multiple probes having the same sequence and detectable label may bind to multiple copies of a corresponding unique nucleic acid sequence at the first segment. The probes bound to the first segment are then removed, for example, by washing, degrading, or photo-bleaching using known methods in the art. The above process is then repeated for each segment in the optical barcode. With successive rounds of hybridization and washing, up to $4^N$ unique sequences can be detected in N rounds using 4 differently colored dye labels. See FIG. 12. For example, the use of four different optically detectable labels requires eight rounds of detection to achieve genome-wide scale (65,536 barcodes), while mixing four colors to produce 10 distinguishable pseudo colors (4 chose 2=6 plus 4 pure colors=10) would enable genome-wide encoding using only five rounds of detection.

The optically detectable labels may be a particular size, shape, color, refractive index, or combination thereof. The optically detectable label should comprise a material and be of a size that can be resolvable using light spectroscopy, non-linear optical microscopy, phase contrast microscopy, fluorescence microscopy, including two-photon fluorescence microscopy, Raman spectroscopy, or a combination thereof. In certain example embodiments, the optically encoded particle may be naturally optically encoded, that is the particle is detectable using one of the above detection means without further modification. In certain other example embodiments, the particle material making up the optically detectable label is amenable to modification such that it can be made optically detectable using one of the above detection means, for example, by fluorescently or colorimetrically labeling the optically detectable label.

The optically detectable labels may comprise fluorophores, colloidal metal particles, nanoshells, nanotubes, nanorods, quantum dots, hydrogel particles, microspheres—such as polystyrene beads—liposomes, dendrimers, and metal-liposome particles. The optically detectable labels may be of any shape including, but not limited to, spherical, string-like, or rod-like. In certain example embodiments, the optically detectable labels are spherical in shape. In certain example embodiments, the optically detectable labels may be formed in a series of pre-defined shapes or sizes in order to distinguish the optically encoded particles by shape or size. In certain example embodiments, the optically detectable labels may have a diameter of approximately 50 nm to approximately 500 µm, or a length of approximately 50 nm to 500 µm.

In one example embodiment, the optically detectable label is a hydrogel particle. The hydrogel particle may be made from, for example, covalently cross-linked PEG with thiol-reactive functional groups, or low melting point agarose functionalized with streptavidin or nucleic acid. In certain example embodiments, the hydrogel particle may be approximately 50 nm to approximately 500 µm in size. In certain example embodiments, the hydrogel particle is fluorescently or colorimetrically labeled. In certain example embodiments, the optical label is incorporated within the hydrogel particle. In certain other example embodiments, the optical label is attached to the surface of the hydrogel particle.

In certain example embodiments, the optically detectable labels are quantum dots. In certain other example embodiments, the quantum dots may be incorporated into larger particles, such as those described above. The quantum dots may be made of semiconductor materials identifiable in the art as suitable for forming quantum dots. Exemplary quantum dots are available for purchase, e.g., from Sigma-Aldrich. The quantum dots may range in size from approximately 2 nm to approximately 20 nm.

In certain example embodiments, the optically detectable label is a colloidal metal particle. The colloidal metal material may include water-insoluble metal particles or metallic compounds dispersed in a liquid, a hydrosol, or a metal sol. The colloidal metal may be selected from the metals in groups IA, IB, IIB and IIIB of the periodic table, as well as the transition metals, especially those of group VIII. Preferred metals include gold, silver, aluminum, ruthenium, zinc, iron, nickel and calcium. Other suitable metals also include the following in all of their various oxidation states: lithium, sodium, magnesium, potassium, scandium, titanium, vanadium, chromium, manganese, cobalt, copper, gallium, strontium, niobium, molybdenum, palladium, indium, tin, tungsten, rhenium, platinum, and gadolinium. The metals are preferably provided in ionic form, derived from an appropriate metal compound, for example the $Al^{3+}$, $Ru^{3+}$, $Zn^{2+}$, $Fe^{3+}$, $Ni^{2+}$ and $Ca^{2+}$ ions.

In certain example embodiments, the optically detectable particles are dendrimers. The dendrimer may be formed using standard methods known in the art. Exemplary dendrimers are available for purchase, e.g., from Sigma-Aldrich. The dendrimer may range in size from 5 nm to 500 nm, depending on the chosen size and length of, e.g., a central core, an interior dendritic structure (the branches), and an exterior surface with functional surface groups.

In certain example embodiments, the probes are fluorescently labeled FISH probes. The probes used herein may be RNA probes, DNA probes, or hybrid RNA/DNA probes. In certain example embodiments, the FISH probes are amine-conjugated oligos coupled to amine-reactive dyes. The sequential binding is carried out using known permeabilization, hybridizing, stripping, and re-hybridizing methods known in the art. In certain example embodiments, the probes are removed between sequential rounds of FISH by incubating the cell or population of cells in a wash solution comprising 60% formamide at 37° C.

In certain example embodiments, the optical barcode encoded in the expressed RNA transcript is detected by hybridization directly to the expressed RNA transcript. In certain other example embodiments, a cDNA copy of the expressed RNA transcript is generated and detection of the optical barcode is achieved by sequential binding to the cDNA copy of the RNA transcript. In certain example embodiments, the cDNA sample is first amplified prior to detection and detection of the optical barcode is achieved by sequential binding of probes to the resulting amplicons, or ligation to a sequencing primer (see e.g. SOLiD sequencing chemistry). In certain example embodiments, amplification is achieved by rolling circle amplification.

In certain example embodiments, the probes comprising the optically detectable labels are bound directly to the optical barcode. In certain other example embodiments, intermediate probes having all the characteristics of the probes labeled with optically detectable labels are used, except the intermediate probes only bind the unique sequences of the optical barcodes and do not carry the optically detectable label. The intermediate probes may be branched probes, with each branch comprising a binding site for a second probe. A second probe comprising a corresponding optically detectable label for each branched probed is then bound to the intermediate probe to generate a detectable signal.

In certain example embodiments, the optical barcode may be detected directly using an in situ sequencing method. In certain example embodiments, the optical barcode sequence is detected using fluorescent in situ RNA sequencing (FIS-SEQ) or in situ mRNA-seq. In certain example embodiments, the mRNA transcript encoding the optical barcode is sequenced. In certain other example embodiments, a cDNA copy of the mRNA is first generated and then sequenced. Alternatively, the optical barcode may be located in a barcode-specific cDNA primer that can be amplified together with the target. See, for example FIG. 1a of Ke et al. Nature Methods 2013, 10(9)857-60.

The invention is further defined with reference to the following numbered clauses:

1. A method for screening cells for genetic modifications comprising:
    culturing a cell or cell population;
    introducing one or more vectors to the cell or cell population, each vector comprising nucleic acid sequences encoding a sequence defining an optical barcode and one or more genetic perturbations, thereby introducing the one or more genetic perturbations and the sequence defining the optical barcode into the cell genome;
    incubating the cells to allow for expression of a RNA transcript comprising the optical barcode, wherein the optical barcode comprises an ordered set of positions, each position comprising a nucleic acid sequence from a set of possible nucleic acid sequences for that position;
    delivering a probe set to the cell or cell population, each probe in the probe set comprising a sequence that hybridizes to one of the possible nucleic acid sequences at the first position of the barcode and an optically detectable label;
    determining the oligonucleotide sequence at the first position of the barcode by detecting the optically detectable label of the probe corresponding to that nucleic acid sequence;
    repeating the delivering and detecting steps for each position in the barcode; and
    identifying the one or more genetic perturbations present in cell or cell population based on the determined barcode sequence.

2. The method of clause 35, further comprising determining an observed phenotype for each cell or cell population by capturing a microscopic image of the cell or cell population; and correlating the observed phenotype to the identified genetic perturbation.

3. The method of clause 35, wherein the RNA transcript comprising the barcode, further comprises a cell localization signal localizing the RNA transcript comprising the barcode to a specific location within the cell.

4. The method of clause 35, wherein the vector further comprises nucleic acid sequences further encoding a nuclease for introducing the one or more genetic perturbations.

5. The method of clause 4, wherein the site-specific nuclease is a RNA-guided DNA endonuclease.

6. The method of clause 5, wherein the RNA-guided DNA endonuclease is dCas9.

7. The method of clause 5, wherein the dCas9 is fused to a second domain.

8. The method of clause 7, wherein the second domain is a nickase.

9. The method of clause 8, wherein the nickase is Fok1.

10. The method of clause 7, wherein the second domain is a catalytically inactive DNA-binding domain.

11. The method of clause 10, wherein the catalytically inactive DNA-binding domain is a transcription activator.

12. The method of clause 6, wherein the dCas9 is catalytically inactive.

13. The method of clause 35, wherein the site-specific nuclease is a zinc-finger nuclease (ZFN) or a transcription activator-like effector nuclease (TALEN).

14. The method of clause 35, wherein the one or more genetic perturbations comprise insertions, deletions, and mutations.

15. The method of clause 35, wherein the RNA transcript comprising the barcode further comprises a premature termination signal to prevent translation of the RNA transcript comprising the barcode.

16. The method of clause 35, wherein each nucleic acid sequence at each position in the barcode is between approximately 100 to approximately 200 nucleotides.

17. The method of clause 35, wherein the barcode comprises 3 to 4 ordered of positions.

18. The method of clause 35, wherein each probe set comprises 3, 4, or 5 distinct optically detectable labels.

19. The method of clause 35, wherein the optically detectable label is a fluorophore.

20. The method of clause 35, wherein the optically detectable label is a quantum dot.

21. The method of clause 35, wherein the optically detectable label is an object of a particular size, shape, color, or combination thereof.

22. The method of clause 35, wherein the cell or cell population comprises a neuronal cell.

23. A method for screening a cell line genetic modifications comprising:
    generating a Cas9 library comprising a set of vectors each vector comprising a sequence defining a barcode, a dCas9 nuclease, and one or more guide RNAs (sgRNA) to introduce one or more genetic perturbations;
    sequencing the Cas9 library to identify the sequence defining the barcode associated with the one or more guide RNAs;
    culturing a cell or cell population;
    delivering a vector from the Cas9 library into the cell or cell population thereby introducing the one or more genetic perturbations and the barcode into the cell or cell population;
    incubating the cell or cell population to allow for expression of an RNA transcript comprising the barcode, wherein the barcode comprises an ordered set of positions, each position comprising a nucleic acid sequence from a set of possible nucleic acid sequences for that position;
    delivering a probe set to the cell or cell population, each probe in the probe set comprising a sequence that hybridizes to one of the possible nucleic acid sequences at the first position of the barcode and an optically detectable label;

determining the nucleotide sequence at the first position of the barcode by detecting the optical label of the probe corresponding to that nucleic acid sequence;

repeating the delivering and detecting steps for each position in the barcode; and identifying the one or more genetic perturbations present in the cell or cell population based on the determined barcode sequence.

24. The method of clause 23, further comprising determining an observed phenotype for each cell or cell population by a capturing a microscope image of the cell or cell population; and correlating the observed phenotype to the identified one or more genetic perturbations.

25. The method of clause 23, wherein the RNA transcript comprising the barcode, further comprises a cell localization signal localizing the RNA transcript comprising the barcode to a specific location within the cell.

26. The method of clause 23, wherein the one or more genetic perturbations comprise insertions, deletions, and mutations.

27. The method of clause 23, wherein the RNA transcript comprising the barcode further comprises a premature termination signal to prevent translation of the RNA transcript comprising the barcode.

28. The method of clause 23, wherein each nucleic acid sequence at each position in the barcode is between approximately 100 to approximately 200 nucleotides.

29. The method of clause 23, wherein the barcode comprises 3 to 4 ordered positions.

30. The method of clause 23, wherein each probe set comprises 3, 4, or 5 distinct optically detectable labels.

31. The method of clause 23, wherein the optically detectable label is a fluorophore.

32. The method of clause 23, wherein the optically detectable label is a quantum dot.

33. The method of clause 23, wherein the optically detectable label is an object of a particular, size, shape, color, or combination thereof.

34. The method of clause 23, wherein the cell or cell population comprises a neuronal cell.

This invention is further illustrated by the following examples, which are not to be construed in any way as imposing limitations upon the scope thereof.

EXAMPLES

Figures 2A, 2B, 2C, 2D:
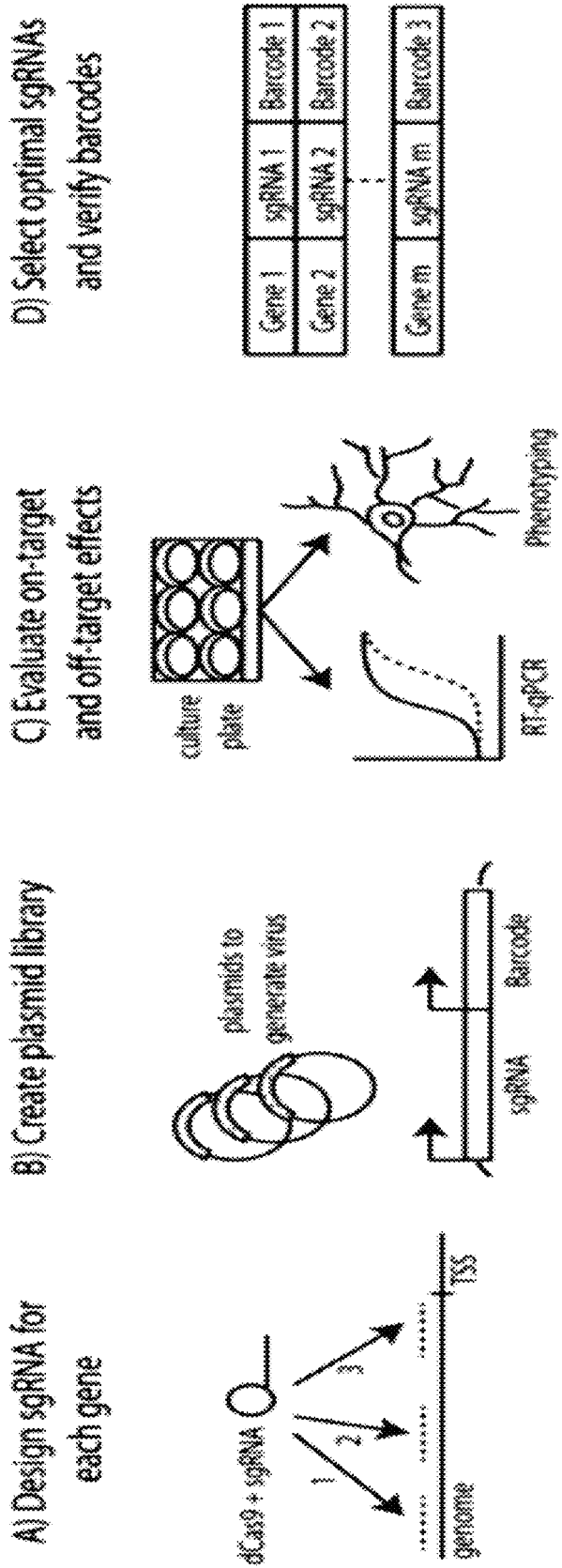
FIG. 2A-2D is another schematic providing an overview of the process of designing optical barcodes and genetic perturbation effectors in accordance with certain example embodiments. Several potential CRISPR guide RNAs (sgRNAs) targeting the genes of interest are cloned into a vector containing a large set of pre-determined optical barcodes. Each single CRISPR sgRNA is validated and arrayed in culture via RT-qPCR to measure efficiency to knockdown expression of the target gene, and cells are imaged to screen against gross off-target effects of any sgRNAs. The optimal sgRNAs targeting each gene are Sanger-sequenced to determine the barcode that tags each sgRNA to create the final library to be used.

CRISPR Transcriptional Effector Library Generation and Validation:

Perturbation reagents are independently optimized and definitively validated since only a small library of engineered viruses is needed to generate a large number of combinations of perturbations (FIG. 2). As shown in the figures, the library is composed of individual viruses carrying a dCas9 transcriptional effector, a CRISPR sgRNA targeted to a candidate gene, a sequence barcode, and green fluorescent protein (GFP). Three sgRNAs for each target gene are chosen (FIG. 2a) and cloned into plasmid vectors carrying a pre-determined sequence barcode with respective promoter architectures for constitutive expression and the genes necessary to generate adeno-associated virus (AAV) [6]. A separate population of cells can be infected with the virus constructed from each plasmid in the library, due to their tractable number.

The virus library and respective sgRNAs are individually surveyed for on-target efficiency and any gross effects of the particular sgRNAs chosen (FIG. 2c). To measure the on-target efficiency of the transcriptional effector, quantitative reverse transcription PCR (RT-qPCR) is a standardized, low cost, and highly efficient assay for induced or silenced transcripts of the target gene in each cell population [7,10]. The optimal sgRNA for a given gene are selected and any sgRNAs that fail to have measurable effects can be redesigned if necessary. sgRNAs with particularly strong gross phenotypic effects are detected in the validation phase (e.g. outliers versus other sgRNAs targeting the same gene or region, presumably due to off-target effects). These failed sgRNAs should be removed from further work. After selecting the optimal sgRNAs, the barcodes carried by each plasmid are verified by Sanger sequencing (FIG. 2d).

Figures 3A, 3B:
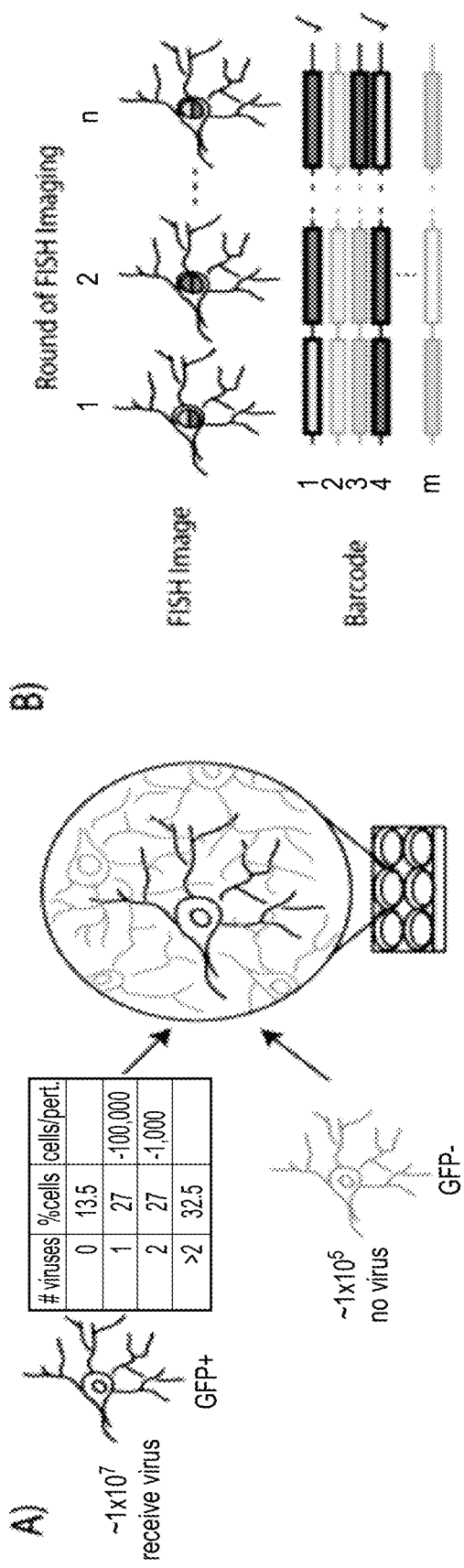
FIG. 3A-3B is a schematic showing the process for efficiently connecting phenotypic outcome to genetic perturbations using optical barcoding and FISH imaging, in accordance with certain example embodiments.

Pooled Screen Design and Cell Phenotyping:

To reveal key phenotypic changes related to overall neuron morphology and synapses between neurons, the following conditions are used: 1) mutant neurons are tested for synapsing with a controlled wild type background (FIG. 3a); 2) a sufficient coverage of single genetic perturbations is used to provide a robust baseline to assess complex genetic interactions; and 3) sufficient cells with the same pair of genetic perturbations are measured to provide robust statistics. Since all cells must interact with the same wild type background cells, it is estimated that in many experiments, infected cells make up around 10% of the cultured population. In the stochastic infection of cells with viruses, it is estimated that around 30% of infected cells will receive 1 virus, 30% a pair of viruses (FIG. 3a). Overall, of all cultured cells, 3% will have a single perturbation, and 3% a pair of perturbations. If 1000 cells of each unique pair must be imaged to obtain robust statistics, a total of 40 plates (~400 million cells) can assay all pairwise perturbations of 100×100 genes (compared to 10,000 wells in existing arrayed formats).

The neuronal phenotypes generated by each genotype are assayed using automated high-throughput fluorescence imaging according to standard protocols (FIG. 3a) [9]. In addition to the dCas9 and sgRNAs, each virus expresses GFP to label the cell body, axon, and dendrites of the cells that received genetic perturbations. The morphology of the labeled cells, such as shape, number, and density of synapses will be assessed [9]. More complex molecular phenotypes such as the localization and expression levels of specific postsynaptic markers can also be surveyed using fusions to fluorescent proteins or immunocytochemistry [9].

Optical Detection of RNA Barcodes:

Since stochastic infection of cells is relied on in a pooled assay format, the exact perturbation received by each infected cell after it has been phenotyped needs to be mapped. This is accomplished by designing the viruses used to deliver the sgRNAs to express sequence barcodes as mRNA distributed over the nuclear area. Fluorescence in situ hybridization of RNA (RNA-FISH) is a robust method for detection of specific mRNA transcripts down to the single molecule level using fluorescence microscopy [14, 15]. Four different color dye labeled ssDNA probes complementary to specific ~20 bp sequences are incubated on permeabilized cells using standard protocols. Any probes that remain bound after washing reveal the presence of RNA with the target sequence. The staining is also reversible; a final chemical melting and washing step returns the sample to its original state, allowing imaging of a new round of probes.

In certain example embodiments, each barcode is designed to have 1 of 4 different sequences corresponding to the different color channels for each round of FISH imaging (FIG. 3b). It is estimated that 7 rounds of 4 color FISH imaging is sufficient for a hypothetical 100×100 genetic screen. The algorithm for identifying barcodes works by deduction. At each round of 4-color imaging, one of ten possible combinations of 2 colors will be recorded, and any barcodes with a color at that round that was not present will be eliminated (FIG. 3b). It is estimated that after 7 rounds, the identity of 80% of cells that received a pair of perturbations can be identified, and 95% after 9 rounds. Any cells with ambiguous perturbations will be removed from subsequent analysis. Since >1000 cells of any given perturbation will be imaged, enough cells remain to still obtain robust phenotype statistics. High content imaging microscopes can typically image each plate in 15 minutes. This barcoding and identification algorithm scales well with the number of perturbations, and works for three-way screens as well; only 3 more rounds of FISH imaging are required for a 1000× 1000 screen or 100×100×100 screen.

Barcode Design and Construction:

In certain example embodiments, barcodes are designed to: 1) contain a sequence of 6 hybridization regions, each with specificity for 1 of 4 different color probes, 2) be verified by Sanger sequencing, 3) be expressed as a single mRNA transcript. The specific probe hybridization sequences will be chosen as random sequences of 20 bases and tested computationally for minimal overlap in binding specificity at room temperature. The barcodes are constructed by synthesizing each 20 bp probe hybridization region and linker region and sequentially ligating, with size selection at each step. At the final step, all barcodes will be sequence-verified. A sequence of six 20 bp sequences and linker regions is well within the length limits of Sanger sequencing and mRNA transcripts.

Fluorescence Imaging and Validation:

The barcoding and imaging technique works regardless of cell type, thus a cell line of low culture maintenance such as the human melanoma derived A375 line will be used. Viruses are constructed according to standard protocols by first transfecting HEK293 cells with plasmids carrying the viral genes barcodes. To test the optimal virus titer for the necessary multiplicity of infection of mean 2 viruses per cell, A375 cells will be infected at a range of titers. [16].

CRISPR Transcriptional Effector Library Design:

Target repression perturbations to the mouse orthologs of the following 6 human genes are designed, all of which have been linked to ASD: DYRK1A, CHD8, GRIN2B, KATNAL2, SYN1, PCDH10 [20, 21, 22]. PSD95, a commonly used excitatory postsynaptic marker, is also targeted as a positive control to yield a clear phenotypic change in high content imaging screen [9]. As a negative control, a sgRNA with no specificity for the human genome is also included. For each gene, 3 positions near the gene transcription are chosen as a start site to target the sgRNA in order to silence the gene. N2a cells are infected with AAV virus carrying the CRISPR machinery and sgRNA, and repression of the target gene is measured by RT-qPCR. Cells are also surveyed for any aberrant phenotypes caused by infection by the virus or activity of the CRISPR transcriptional effector. The sgRNAs that optimally repress target genes make up the final sgRNA set.

Cell phenotyping: The assessment of phenotype used in previous high throughput screens are adopted by measuring general synapse morphology as well as the expression of two postsynaptic markers. In addition to the CRISPR machinery and RNA barcodes, the viruses also express GFP, allowing for tracing of the whole cell body of infected neurons. Tracing the cell body with fluorescent GFP images allows synapse number, area, density, and eccentricity to be assessed. Using standard immunocytochemistry, Psd95, an excitatory postsynaptic marker [23], and Gephyrin (Gphn), an inhibitory postsynaptic marker [24], are also stained to assess the corresponding expression levels and density of puncta at synapses [9]. Images are collected using a Nikon Ti-Eclipse fluorescence microscope or the Acumen Ex3 High Content Imaging platform. All image analysis is completed using CellProfiler software [25].

Barcodes are designed to minimize secondary structure and avoid cross-hybridization with endogenous RNA using well-tested algorithms. The modular barcode assembly strategy uses a common type IIs restriction site introduced via an initial PCR reaction to allow pooled restriction digest, sticky-end ligation, and purification. Thus, the same procedure is used to create individual and pooled barcodes at a moderate, fixed cost. Introducing several randomized nucleotides within each barcode as a unique identifier permits inexpensive shotgun sequencing of barcoded plasmids to match barcodes to sgRNAs.

Figure 4:
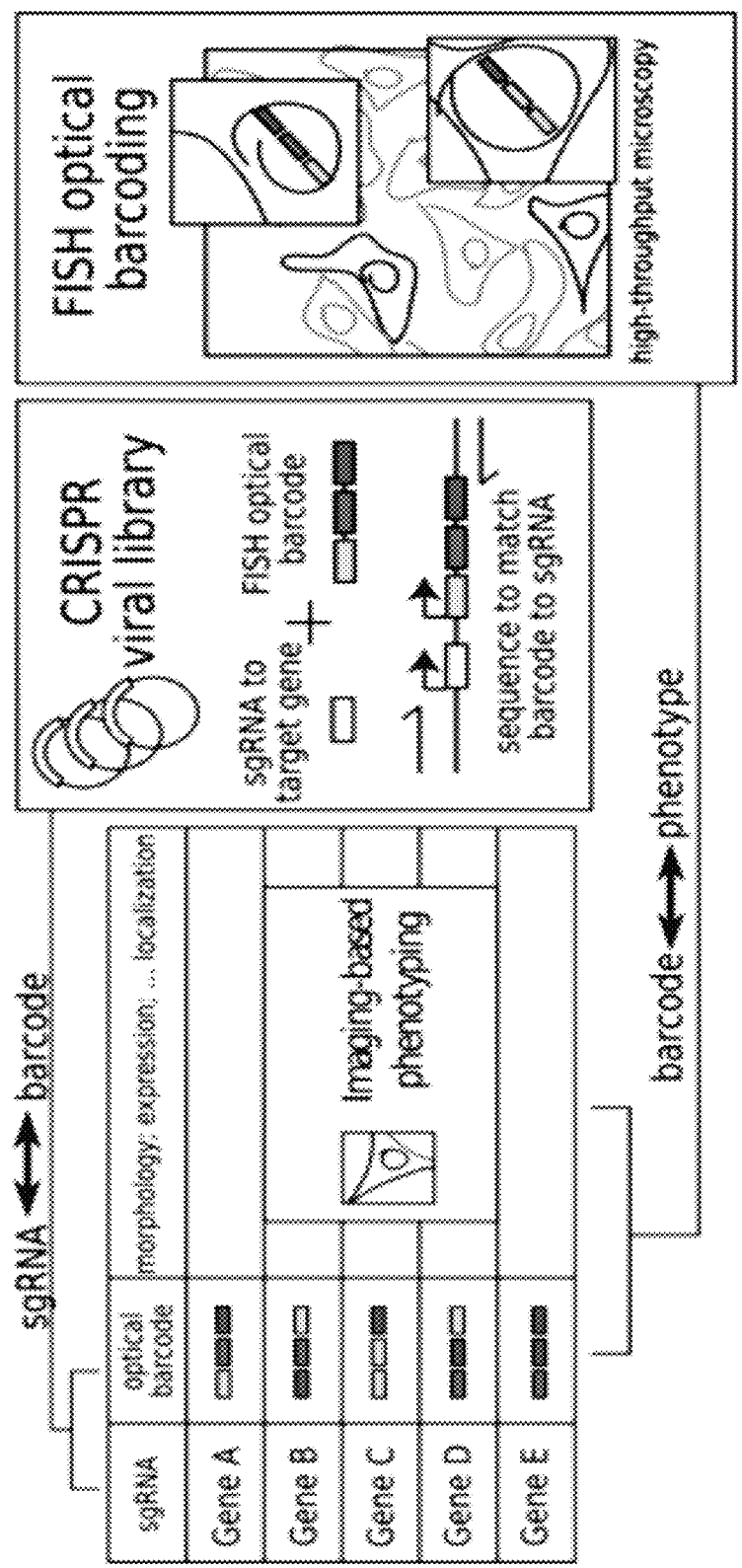
FIG. 4 is an alternative schematic showing the process for efficiently connected phenotypic outcome to genetic perturbations using optical barcoding and FISH imaging, in accordance with certain example embodiments. Each sgRNA in a pooled screen is matched to an optical barcode. Information-rich imaging-based phenotypes are collected for thousands of cells per sgRNA. Optical barcodes are combinatorially assembled and cloned into an existing lentiviral CRISPR library. The constructs are sequenced to match sgRNAs to barcodes. Due to the random nature of pooled cloning, a 10-fold excess of barcodes to sgRNAs is required to ensure >95% of sgRNAs are unambiguously encoded. Optical barcodes are read out by sequential FISH at the end of the screen, prior to fluorescent staining and phenotyping.
Figures 5A, 5B, 5C, 5D:
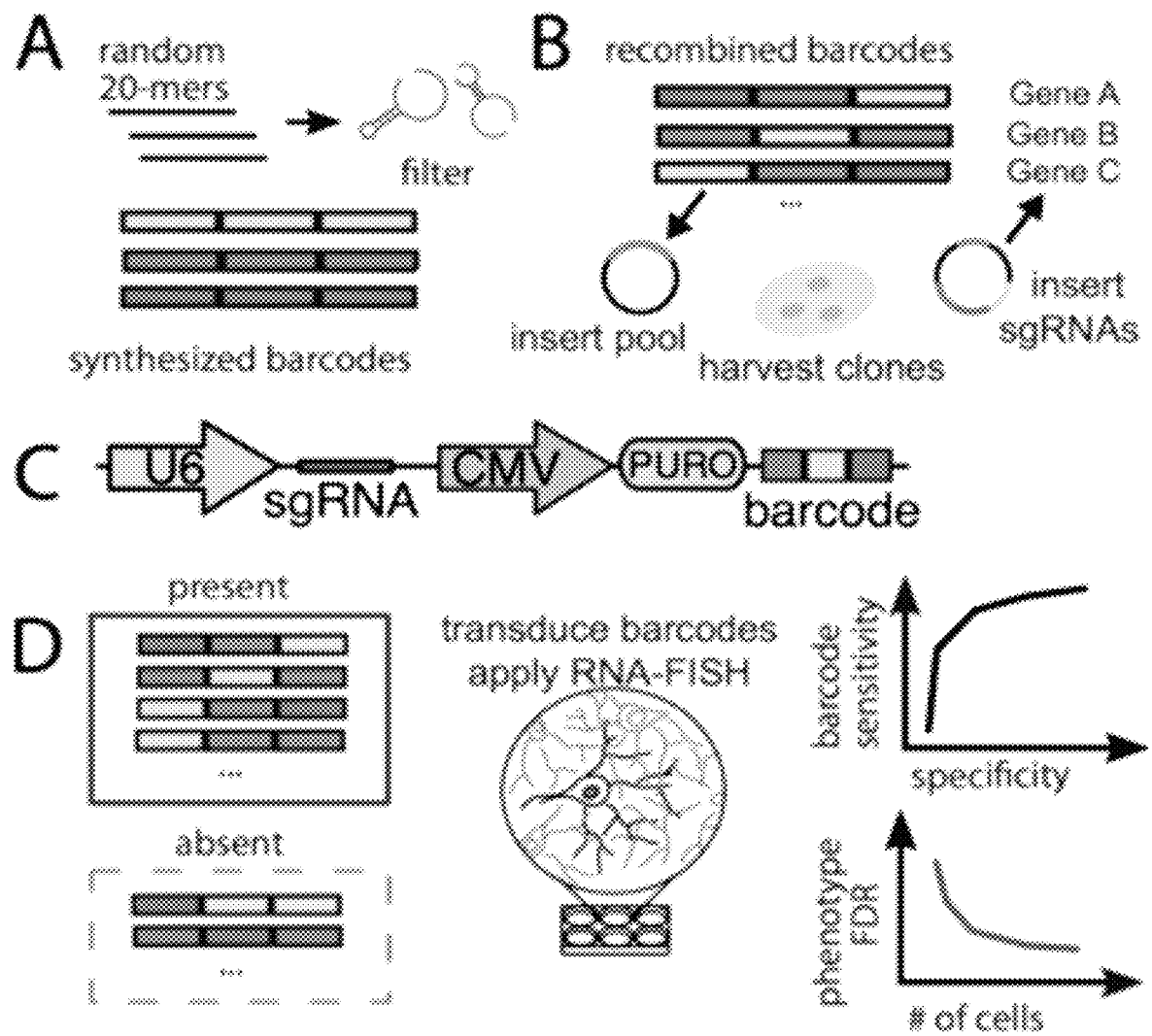
FIG. 5A-FIG. 5D is a schematic showing a process for synthesizing and assessing optically encoded sgRNA libraries, in accordance with certain example embodiments. A modular barcode assembly strategy uses a common type IIs restriction site introduced via an initial PCR reaction to allow pooled restriction digest, sticky-end ligation, and purification. Thus the same procedure is used to create individual and pooled barcodes at a moderate, fixed cost. Introducing several randomized nucleotides within each barcode as a unique identifier permits inexpensive shotgun sequencing of barcoded plasmids to match barcodes to sgRNAs.
Figure 6A:
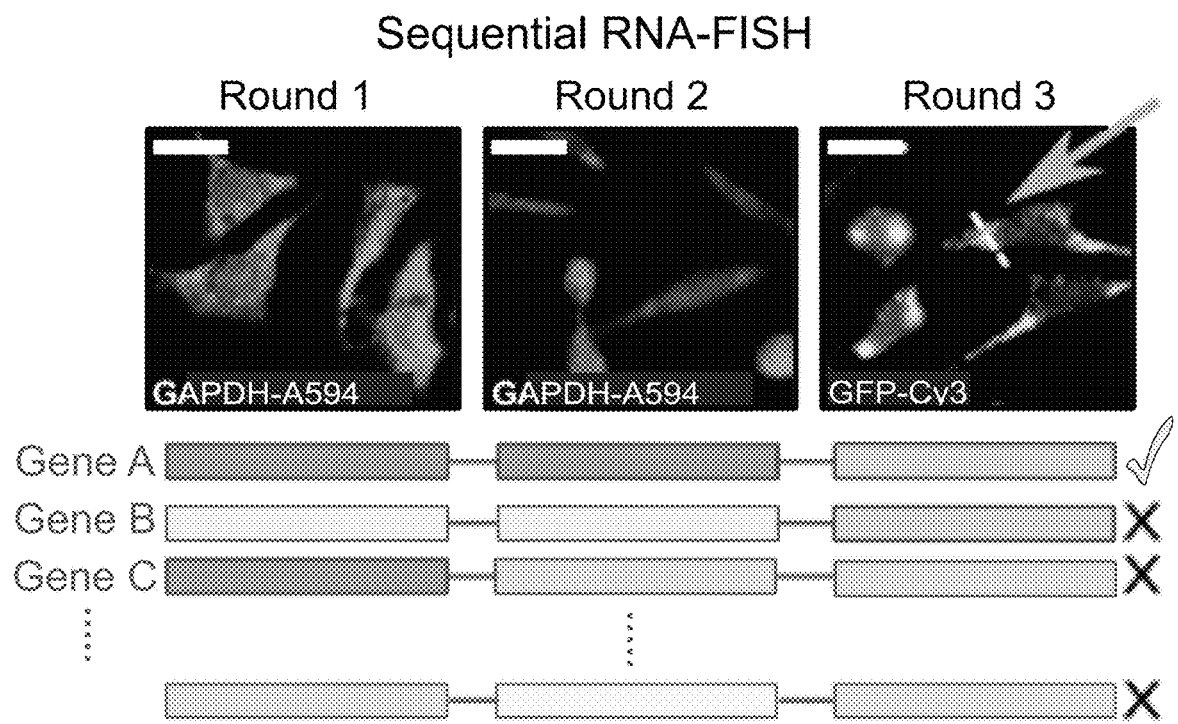
FIG. 6A-FIG. 6C provide a set of images and corresponding graph summarizing data observed from analysis of those images.
Figure 6B:
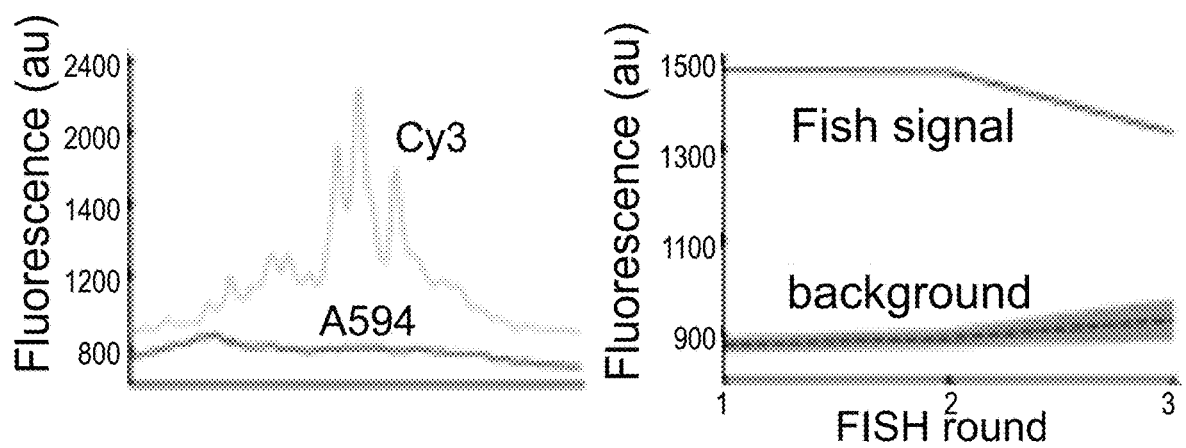
Figure 6C:
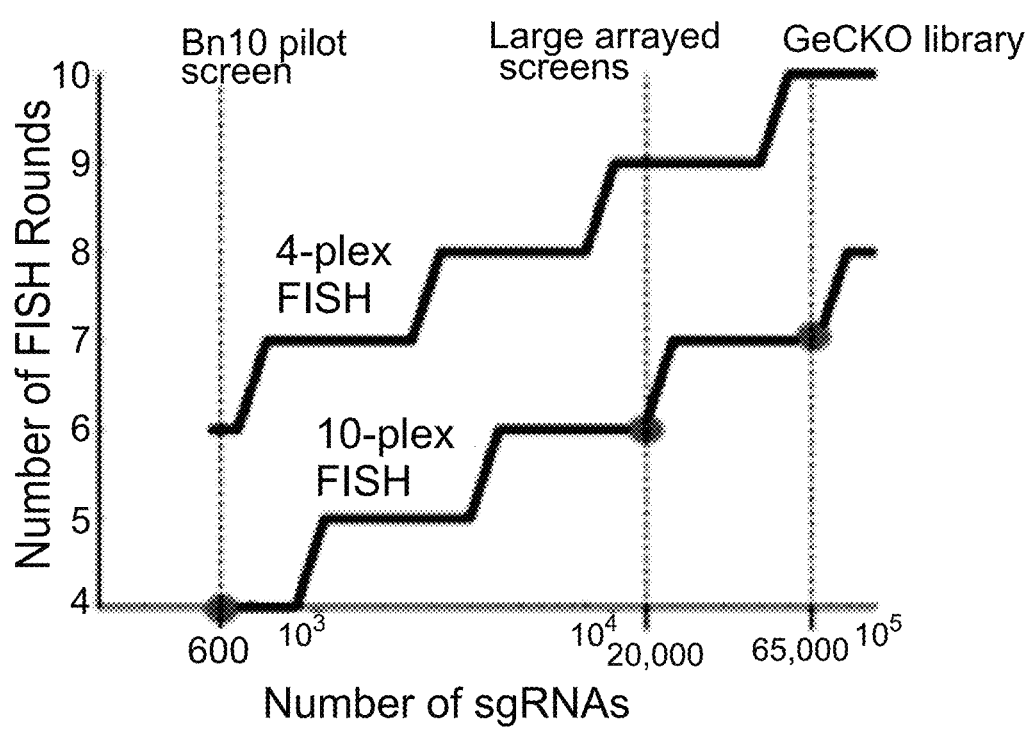
Figures 7A, 7B, 7C:
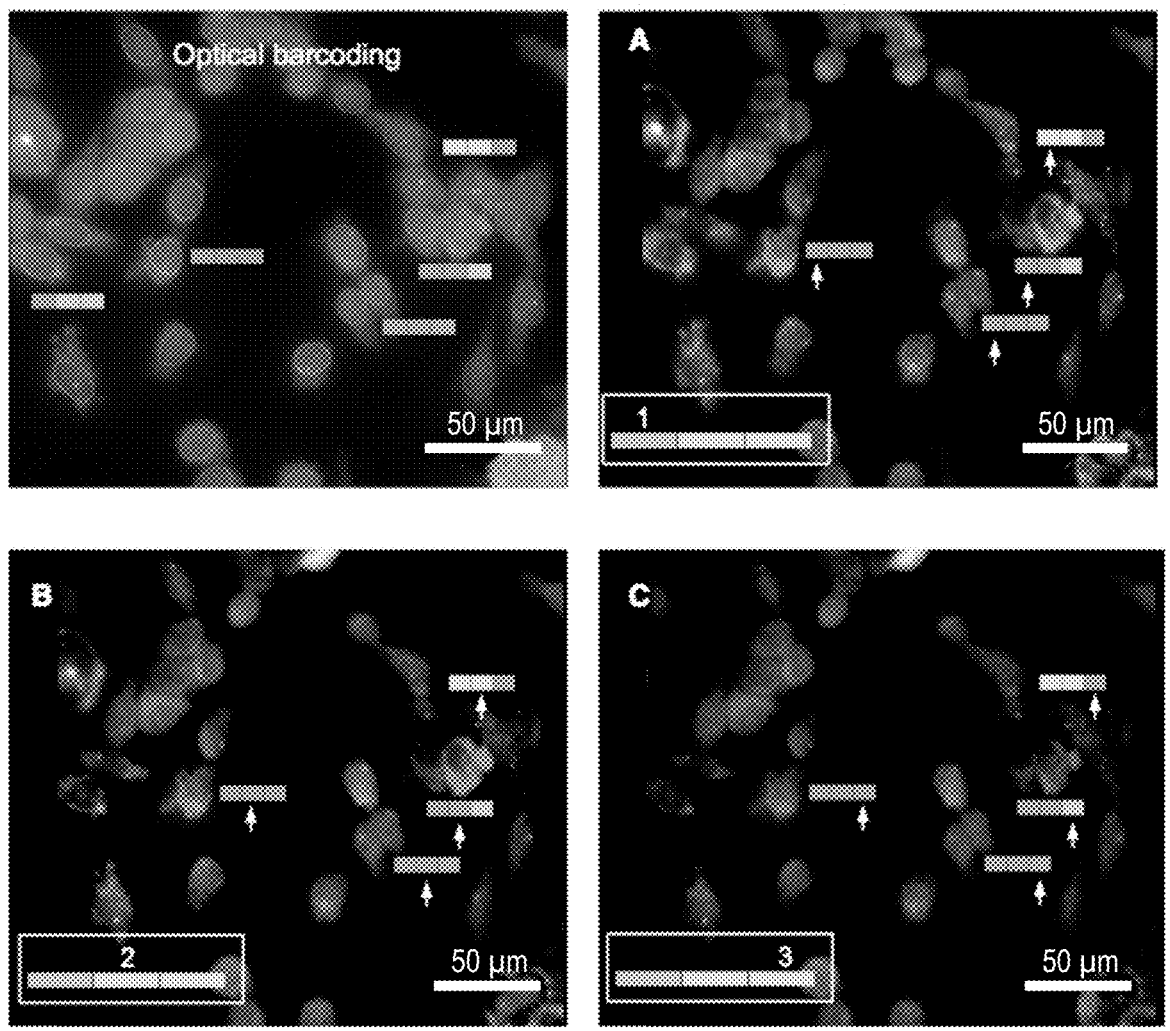
FIG. 7A-FIG. 7C provides a panel of images detecting an example readout of optical barcodes using fluorescent imaging in accordance with certain example embodiments. Schematics of the optical barcode are layered next to cells that received that particular barcode and detection of different probes over sequential rounds of FISH are shown, with the fluorescent label detected in each cell for each round as dictated by the order of the segments in the optical barcode.
Figures 8A, 8B, 8C:
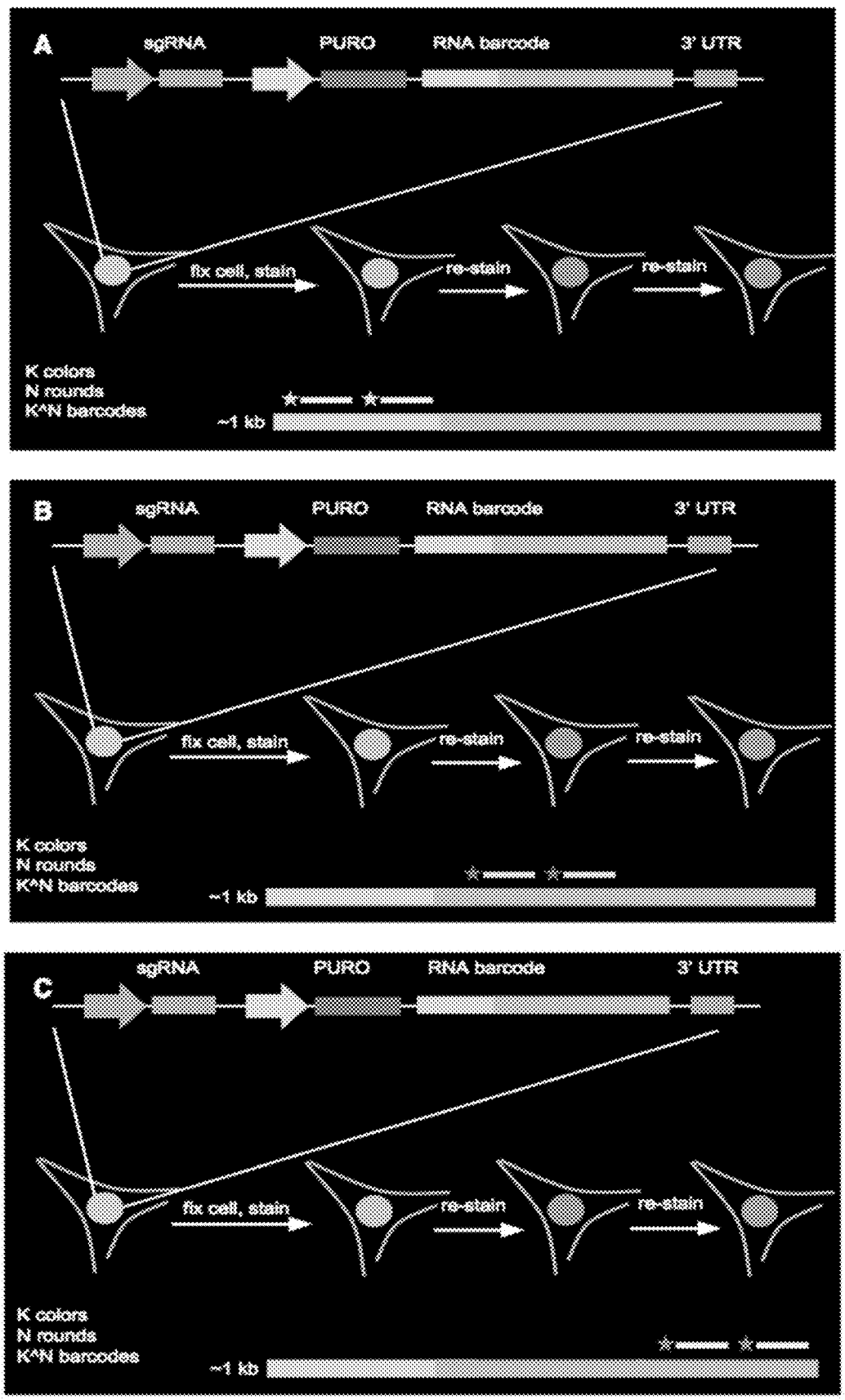
FIG. 8A-FIG. 8C provides panels of schematics showing the process of sequentially binding probes recognizing different segments on an example optical barcode construct.

To generate a barcode pool, the precursor oligos are pooled before assembling and inserting the barcode pool into the lentiGuide-Puro vector backbone. The subsets of sgRNAs targeting genes regulating mitochondrial density and function are then cloned to create bona fide barcoded vector libraries for use in a pilot screen. Each library is shotgun sequenced to define a "hash table" mapping optical barcodes to sgRNAs in that particular library (FIG. 4). By selecting a fixed number of colonies during cloning, the number of barcodes per sgRNA can effectively be controlled. Note that due to the random cloning step, an excess of RNA barcodes is provided to ensure a unique mapping for each sgRNA, with a 10-fold excess of barcodes being provided to ensure >95% of guides are included.

Figure 9:
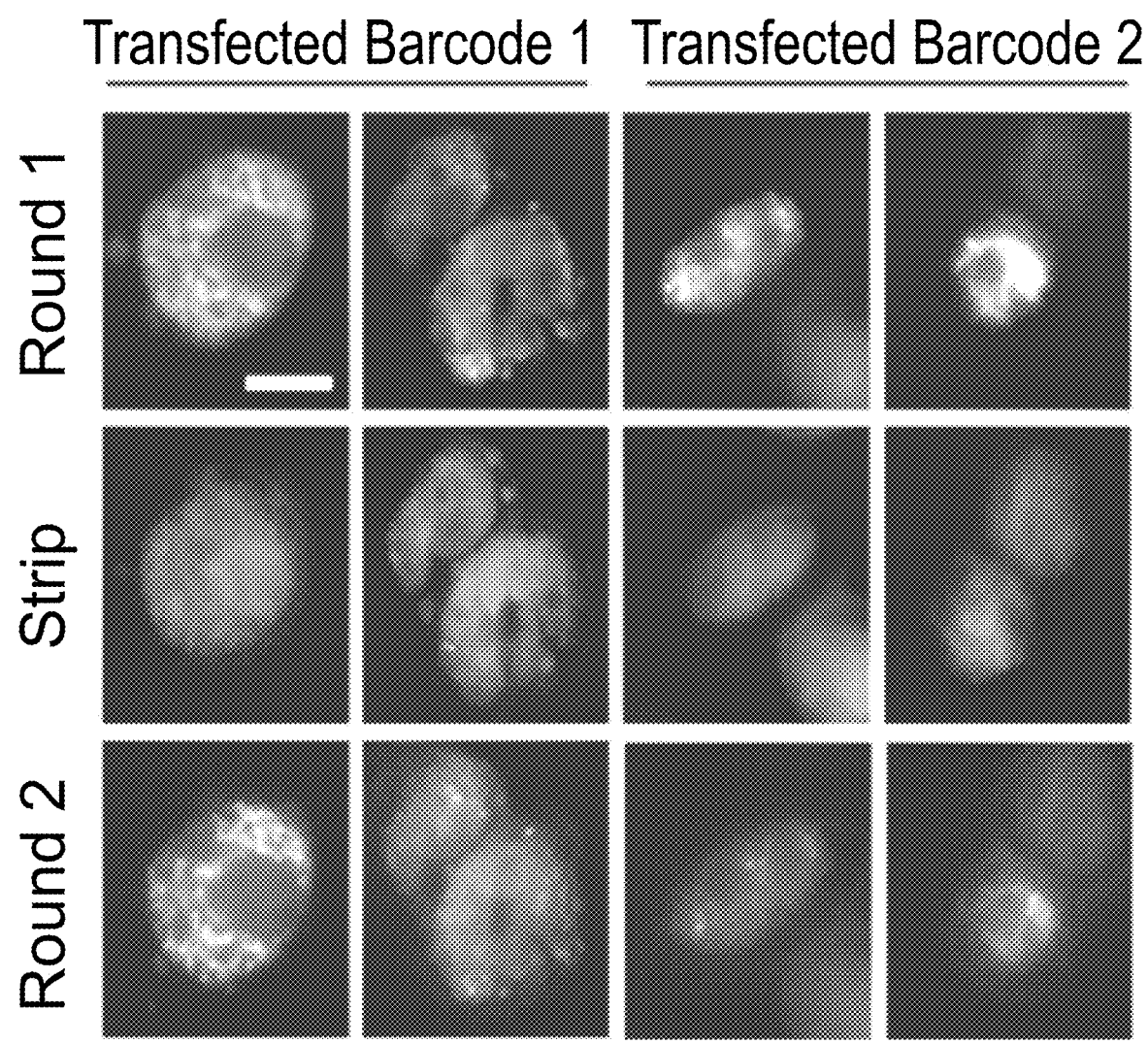
FIG. 9 is a panel of fluorescent images showing the results of two rounds of RNA-FISH against nuclear targeted synthetic optical barcodes transfected into HeLa cells.
Figure 10:
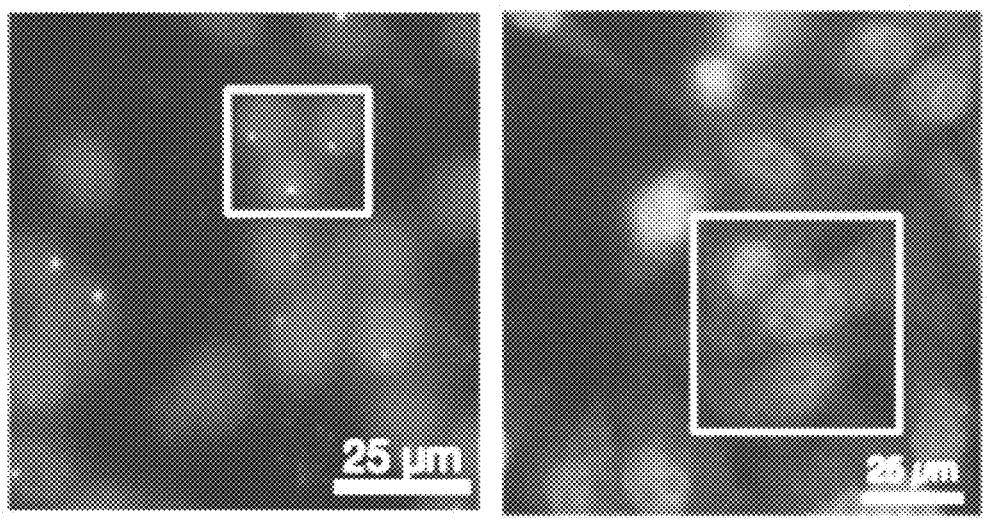
FIG. 10 is a series of fluorescent images demonstrating that optical barcode expression is readily visibly by RNA-FISH at low magnification due to strong sub-cellular localization.
Figure 11:
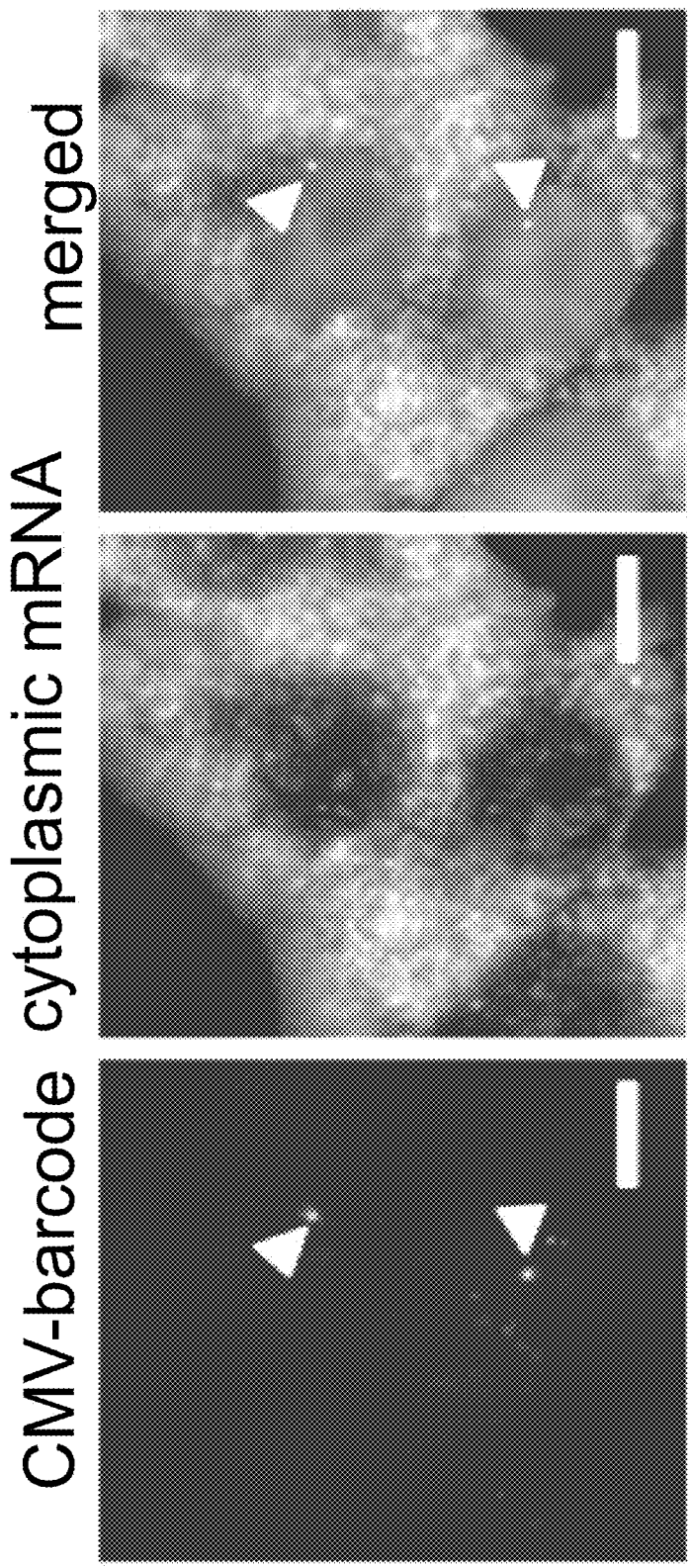
FIG. 11 is a series of fluorescent images showing that sub-nuclear localization of optical barcodes allows simultaneous staining in the cytosol.
Figure 12:
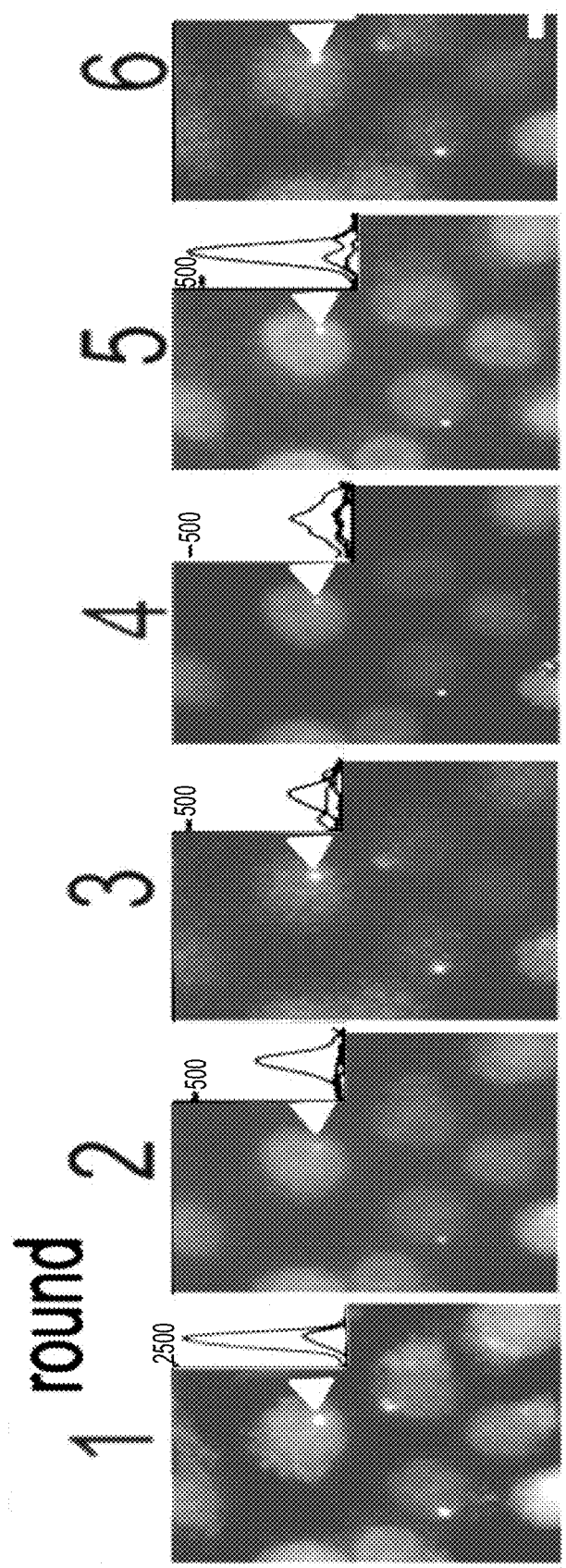
FIG. 12 is a series of fluorescent images showing the results observed over 6 rounds of 3 color RNA-FISH, in accordance with certain example embodiments.
Figure 13:
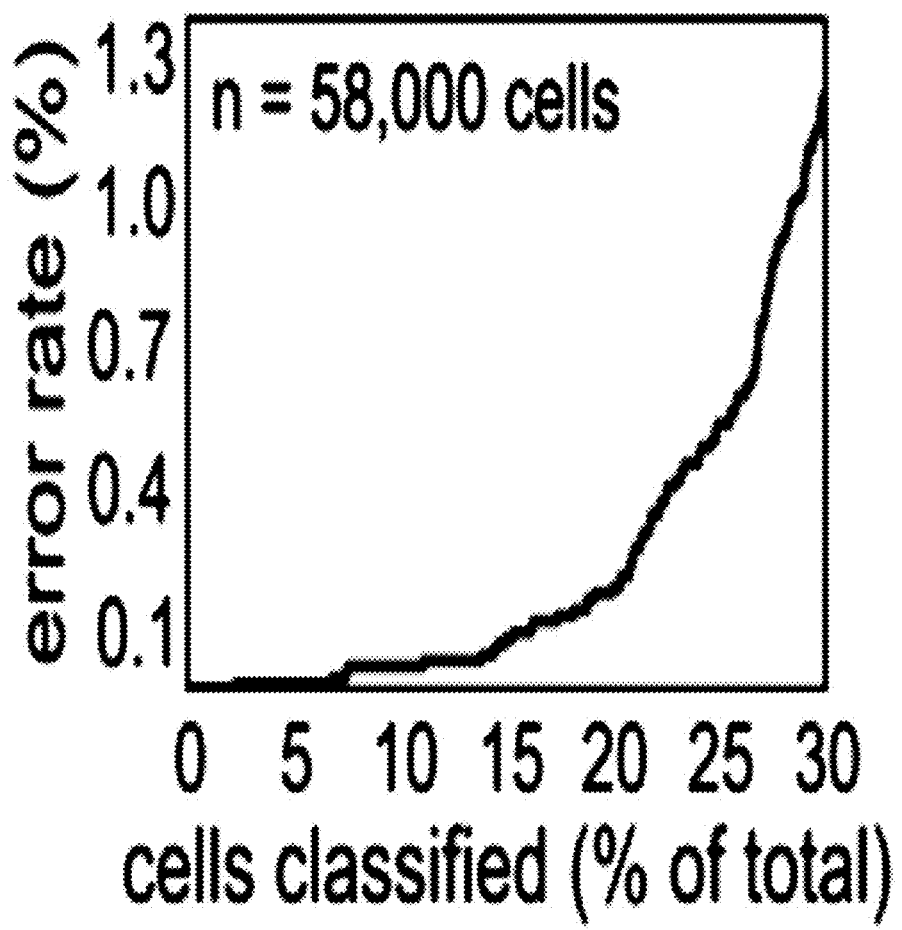
FIG. 13 is a graph showing the percent of cells classified during the 6 rounds of 3 color RNA-FISH shown in FIG. 12, in accordance with certain embodiments.
Figure 14:
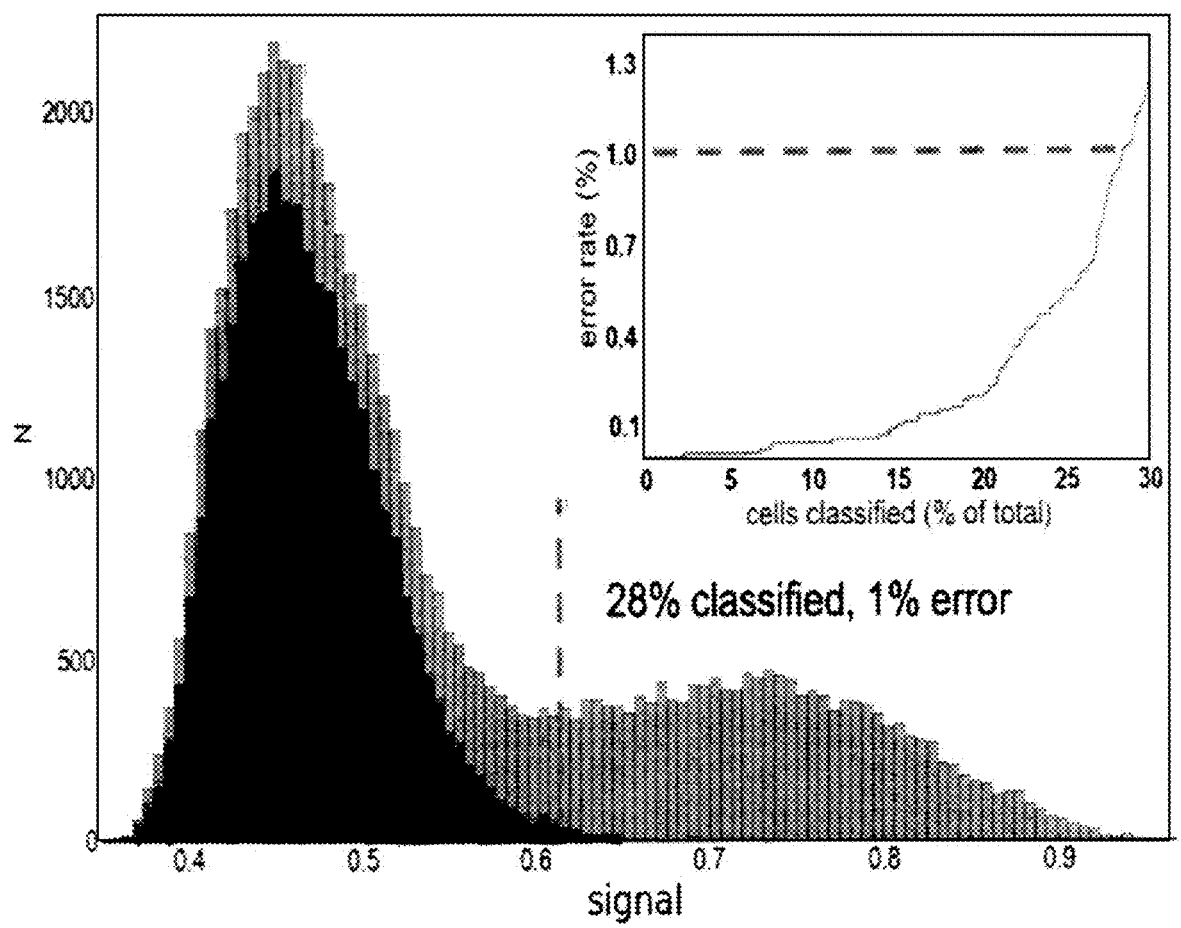
FIG. 14 is a graph showing the results of an experiment measuring barcoding accuracy. A barcode set containing 14 out of 27 possible barcodes was introduced into A375 cells using lentivirus at a low multiplicity of infection. Cells were classified by barcode and scored by signal level. The histogram shows the signal level for cells with all barcodes in gray, and cells with 13 absent barcodes in (black). Note that excluded barcodes are called in cells with low signal. Barcoding accuracy as a function of the stringency of analysis is shown in the inset plot. The dashed lines show that with a cutoff of the top 28% of cells ranked by signal level, the barcoding error rate, as represented by fraction of absent barcodes assigned, is less than 1% so 99% of cells analyzed are accurately barcoded.
Figure 15:
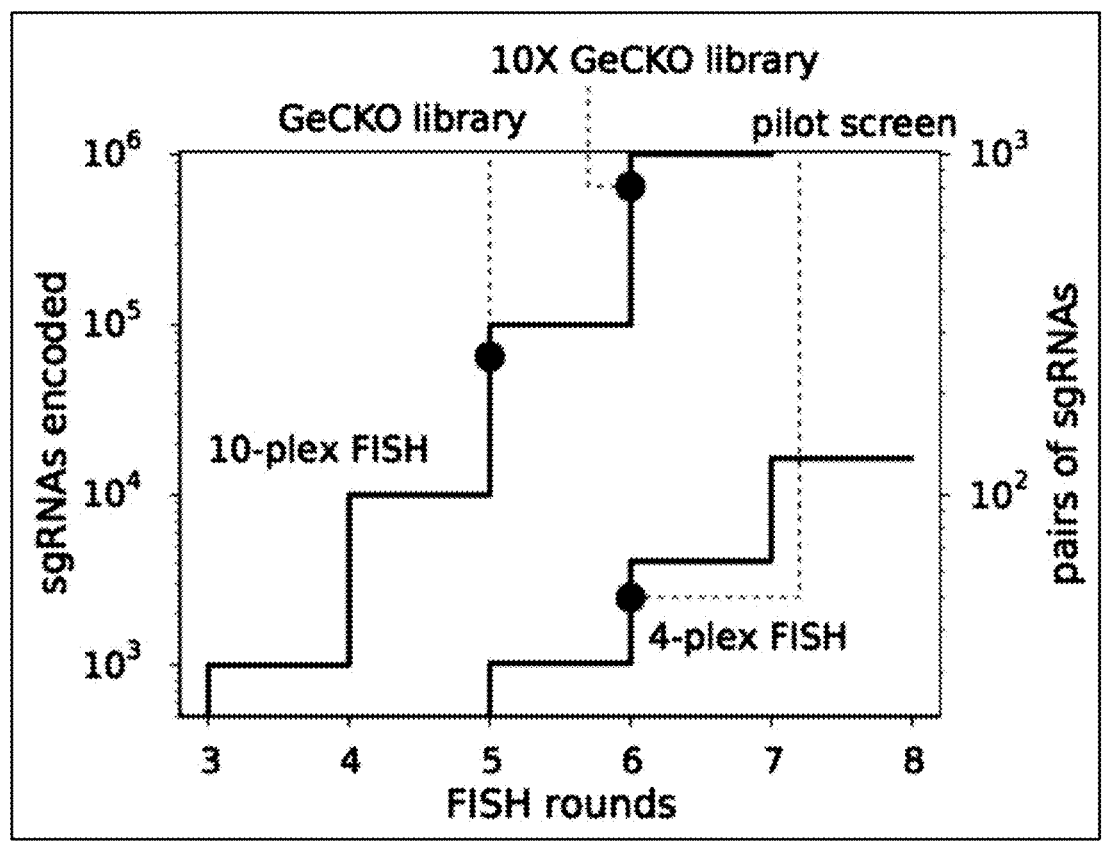
FIG. 15 is a graph showing that the number of optical barcodes provided by sequential probing of the optical barcodes grows as $N^K$, where N is the number of colors distinguishable by fluorescence, including pseudo-colors (e.g. green, green+blue, . . . ) and K is the number of rounds of multi-color FISH. Note that with 10 pseudo-colors, only 6 rounds of FISH are required to achieve genome-wide scale.

FIG. 9 shows two rounds of sequential RNA-FISH against nuclear targeted synthetic barcodes transfected into HeLa cell according to certain example embodiments disclosed herein. Images show the same cell nuclei after hybridization, stripping and re-hybridization (round 1 Cy3, round 2: Alexa 594; scale bar 10 µm; blue signal in each frame is DAPI that marks nuclei). This demonstrates the ability to target barcodes to the nucleus and re-probe the same exact RNA molecules. FIG. 10 demonstrates that RNA barcode expression is readily visible by RNA-FISH at low magnification due to strong sub-nuclear localization, seen with CMV promoter (left panel) but not EF1a promoter (right). FIG. 11 demonstrates that sub-nuclear localization allows simultaneous staining of the cytosol, in this case GAPDH mRNA (scale bar 10 µm). FIG. 12 shows results from 6 rounds of 3 color RNA-FISH, which can distinguish 729 barcodes ($3^6=729$ unique barcodes, e.g. 729 genes; scale bar 20 µm). FIG. 13 shows that barcodes can be distinguished with high specificity across many of the cells imaged in the experiment shown in FIG. 12.

Various modifications and variations of the described methods, pharmaceutical compositions, and kits of the disclosure will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

All publications, patents, and patent applications mentioned herein are incorporated by reference to the same extent as if each individual publication, patent or patent application was specifically and individually indicated to be incorporated by reference in its entirety. In the event of there being a difference between definitions set forth in this application and those in documents incorporated herein by reference, the definitions set forth herein control.

REFERENCES

1. Szatmari P. Heterogeneity and the genetics of autism. Journal of Psychiatry and Neuroscience, 24(2): 159, 1999.
2. O'Roak B. J., et al. Multiplex Targeted Sequencing Identifies Recurrently Mutated Genes in Autism Spectrum Disorders. Science, 338(6114): 1619-1622, 2012.
3. O'Roak B. J., et al. Sporadic autism exomes reveal a highly interconnected protein network of de novo mutations. Nature, 485(7397): 246-250, 2012.
4. Zhang F., et al. Multimodal fast optical interrogation of neural circuitry. Nature, 446(7136): 633-639, 2007.
5. Hochbaum, D. R., et al. All-optical electrophysiology in mammalian neurons using engineered microbial rhodopsins. Nature Methods, 11(8): 825-833, 2014.
6. Sanjana N. E., Shalem, O., & Zhang, F. Improved vectors and genome-wide libraries for CRISPR screening. Nature Methods, 11(8): 783-784, 2014.
7. Sanjana N. E., et al. A transcription activator-like effector toolbox for genome engineering. Nature Protocols, 7(1): 171-192; 2014.
8. Broad Institute Specialized Service Facility Pricing, July 2014.
9. Nieland T. J. F., et al. High Content Image Analysis Identifies Novel Regulators of Synaptogenesis in a High-Throughput RNAi Screen of Primary Neurons. PLoS One, 9(3): e91744, 2014.
10. Shalem O.*, Sanjana N E.*, et al. Genome-Scale CRISPR-Cas9 Knockout Screening in Human Cells. Science 343(6166): 84-7, 2013.
11. Melnikov A, et al. Systematic dissection and optimization of inducible enhancers in human cells using a massively parallel reporter assay. Nat Biotech 30(3):217-7, 2012.
12. We assume the following costs for a 100×100 screen: cloning and virus library optimization: $3000; cell culture: $2000. We estimate imaging with 7 rounds of FISH staining at roughly 2 hours/plate, so 10 plates can be imaged per day using an automated high content imaging microscope. Assuming $1000/day imaging cost, and 50 plates used in our 100×100 screen, total imaging cost is $5000. Therefore, we estimate total costs to be around $10,000.
13. Larson MH, et al. CRISPR interference (CRISPRi) for sequence-specific control of gene expression. Nature Protocols 8(11): 2180-96, 2013.
14. Batish M, et al. Single molecule imaging of RNA in situ. Methods Mol Bio 714:3-13, 2011.
15. Kallioniemi O. P., et al. ERBB2 amplification in breast cancer analyzed by fluorescence in situ hybridization. Proc Nat Acad Sci 89(12):5321-5, 1992.
16. TTP Labtech. Acumen cellista. ttplabtech.com/cell-imaging/acumen/, Sep. 30, 2014.
17. Tamiji J, et al, Prostaglandin E2 and misoprostol induce neurite retraction in Neuro-2a cells. Biochem Biophys Res Commun 398(3):450-6, 2010.
18. Lin C H, et al. Activation of Trim17 by PPARγ is involved in Di (2-ethylhexyl)phthalate (DEHP)-induced apoptosis in Neuro-2a cells. Toxicol Lett 206(3):245-51, 2011.
20. Willsey et al. Coexpression Networks Implicate Human Midfetal Deep Cortical Projection Neurons in the Pathogenesis of Autism. Cell 155(5):997-1007, 2013.
21. King I F, et al. Topoisomerases facilitate transcription of long genes linked to autism. Nature 501(7465):58-62, 2013.
22. Devlin B & Scherer S W. Genetic architecture in autism spectral disorder. Curr Opin Genet Dev 22(3):229-37, 2012.
23. Kornau H C, Schenker L T, Kennedy M B, Seeburg P H. Domain interaction between NMDA receptor subunits and the postsynaptic density protein PSD-95. Science 269: 1737-1740, 1995.
24. Lionel A C, Vaags A K, Sato D, Gazzellone M J, Mitchell E B, et al. Rare exonic deletions implicate the synaptic organizer Gephyrin (GPHN) in risk for autism, schizophrenia and seizures. Human Molecular Genetics 22: 2055-2066, 2013.
25. Carpenter A E, Jones T R, Lamprecht M R, Clarke C, Kang I H, Friman O, Guertin D A, Chang J H, Lindquist R A, Moffat J, Golland P, Sabatini D M. CellProfiler: image analysis software for identifying and quantifying cell phenotypes. Genome Biology 7:R100, 2006.

What is claimed is:

1. A method for screening cells comprising:
   culturing a cell or population of cells in one or more discrete volumes;
   introducing (a) one or more vectors into the cell or cell population, each vector comprising nucleic acid sequences encoding (i) a guide RNA (sgRNA) and (ii) one or more optical barcodes, wherein a different optical barcode is assigned to each sgRNA; and (b) a catalytically inactive Cas9 (dCas9) fused to a second domain, wherein the second domain is a nickase, a transcriptional activator, a transcriptional repressor, a recombinase, a transposase, a DNA methyltransferase, or a histone methyltransferase;
   incubating the cells to allow for expression of RNA comprising the one or more optical barcodes, wherein each optical barcode comprises a set of ordered segments, each segment comprising a nucleic acid sequence from a set of possible nucleic acid sequences for that particular segment and wherein the RNA comprising the barcode further comprises a premature termination signal to prevent translation of the RNA comprising the barcode; and
   detecting the one or more optical barcodes in the RNA to identify the one or more sgRNA present in the cell or cell population.

2. The method of claim 1, wherein detecting the one or more optical barcodes comprises:
   delivering a probe set to the cell or cell population, each probe in the probe set comprising a sequence that hybridizes to one of the possible nucleic acid sequences at the first segment of the optical barcode on the RNA, wherein different probe sequences are labeled with different optically detectable labels such that each nucleic acid sequence at the first segment of the optical barcode is labeled with a different optically detectable label;

determining the nucleotide sequence at the first segment of each barcode by detecting the optically detectable labels; and repeating the delivering and determining steps for each segment in the barcode to detect all remaining segments in the optical barcode, wherein the order in which the probes in the probe set bind to the segments of the optical barcode identify each optical barcode and thereby identify the one or more sgRNAs introduced into each cell or cell population.

3. The method of claim 2, wherein each probe set comprises 3, 4, or 5 distinct optically detectable labels.

4. The method of claim 2, wherein the optically detectable label is a quantum dot.

5. The method of claim 2, wherein the optically detectable label is an object of a particular size, shape, color, or combination thereof.

6. The method of claim 1, wherein detecting the one or more optical barcodes comprises:

delivering an intermediate probe set to the cell or cell population, each probe in the probe set comprising a sequence that hybridizes to one of the possible nucleic acid sequences at the first segment of the optical barcode on the RNA;

delivering a second probe set that comprises probes that bind to the intermediate probes, the probes in the second probe set comprising an optically detectable label;

determining the nucleotide sequence at the first segment of each barcode by detecting the optically detectable labels; and repeating the delivering and determining steps for each segment in the barcode to detect all remaining segments in the optical barcode, wherein the order in which the probes in the probe set bind to the segments of the optical barcode identify each optical barcode and thereby identify the one or more sgRNAs introduced into each cell or cell population.

7. The method of claim 6, wherein the intermediate probes are branched probes that facilitate the binding of multiple probes from the second probe set to a single intermediate probe.

8. The method of claim 1, wherein the RNA comprising the barcode further comprises a nuclear localization signal, and wherein the nuclear localization signal is a 3' untranslated region (UTR) stem loop from MALAT1 lncRNA transcript.

9. The method of claim 1, wherein the dCas9 fused to the second domain is introduced into the cell or cell population by the one or more vectors, and wherein the one or more vectors further comprises a nucleic acid sequence encoding the dCas9 fused to the second domain.

10. The method of claim 9, further comprising generating, prior to the introducing, a set of gateway vectors, the gateway vectors comprising a sgRNA and corresponding optical barcode assigned to each sgRNA such that the sgRNA and optical barcode are adjacent to one another; and identifying each sgRNA and optical barcode pair using short-read DNA sequencing.

11. The method of claim 1, wherein the second domain is a nickase.

12. The method of claim 11, wherein the nickase is Fok1.

13. The method of claim 1, wherein the optical barcode further comprises a unique molecular identifier (UMI), and each sgRNA sequence comprises a barcode-UMI specific homology sequence to facilitate one to one cloning of sgRNAs to corresponding optical barcodes.

14. The method of claim 1, wherein the optical barcode further comprises a unique molecular identifier (UMI).

15. The method of claim 14, further comprising sequencing the UMI and optical barcode to identify the UMI assigned to each optical barcode thereby allowing short sequencing of the UMI to identify the optical barcode associated with each vector and sgRNA encoded by that vector.

16. The method of claim 1, further comprising sequencing the one or more vectors to identify the optical barcode assigned to each sgRNA.

17. A method for screening cells for one or more genetic perturbations comprising:

culturing a cell or population of cells in one or more discrete volumes;

introducing one or more vectors into the cell or cell population, each vector comprising nucleic acid sequences encoding (i) one or more optical barcodes, (ii) one or more genetic perturbations, and (iii) a zinc finger nuclease (ZFN) or a transcription activator-like effector nuclease (TALEN), thereby introducing the one or more genetic perturbations and the sequence encoding the one or more optical barcodes into the cell, wherein a different optical barcode is assigned to each genetic perturbation;

incubating the cells to allow for expression of RNA comprising the one or more optical barcodes, wherein each optical barcode comprises a set of ordered segments, each segment comprising a nucleic acid sequence from a set of possible nucleic acid sequences for that particular segment and wherein the RNA comprising the barcode further comprises a premature termination signal to prevent translation of the RNA comprising the barcode; and detecting the one or more optical barcodes in the RNA to identify the one or more genetic perturbations present in the cell or cell population.

18. The method of claim 17, wherein detecting the one or more optical barcodes comprises:

delivering a probe set to the cell or cell population, each probe in the probe set comprising a sequence that hybridizes to one of the possible nucleic acid sequences at the first segment of the optical barcode on the RNA, wherein different probe sequences are labeled with different optically detectable labels such that each nucleic acid sequence at the first segment of the optical barcode is labeled with a different optically detectable label;

determining the nucleotide sequence at the first segment of each barcode by detecting the optically detectable labels; and repeating the delivering and determining steps for each segment in the barcode to detect all remaining segments in the optical barcode, wherein the order in which the probes in the probe set bind to the segments of the optical barcode identify each optical barcode and thereby identify the one or more genetic perturbations introduced into each cell or cell population.

19. The method of claim 17, wherein detecting the one or more optical barcodes comprises:

delivering an intermediate probe set to the cell or cell population, each probe in the probe set comprising a sequence that hybridizes to one of the possible nucleic acid sequences at the first segment of the optical barcode on the RNA;

delivering a second probe set that comprises probes that bind to the intermediate probes, the probes in the second probe set comprising an optically detectable label;

determining the nucleotide sequence at the first segment of each barcode by detecting the optically detectable labels; and repeating the delivering and determining steps for each segment in the barcode to detect all remaining segments in the optical barcode, wherein the order in which the probes in the probe set bind to the segments of the optical barcode identify each optical barcode and thereby identify the one or more genetic perturbations introduced into each cell or cell population.

20. The method of claim 19, wherein the intermediate probes are branched probes that facilitate the binding of multiple probes from the second probe set to a single intermediate probe.

21. The method of claim 17, wherein the optical barcode further comprises a unique molecule identifier (UMI).

22. The method of claim 21, further comprising sequencing the UMI and optical barcode to identify the UMI assigned to each optical barcode thereby allowing short sequencing of the UMI to identify the optical barcode associated with each vector and genetic perturbation encoded by that vector.

23. The method of claim 17, wherein the sequence encoding the one or more genetic perturbations comprises one or more nucleotide insertions, deletions, or substitutions.

24. The method of claim 17, further comprising sequencing the one or more vectors to identify the optical barcode assigned to each genetic perturbation.

25. The method of claim 1 or claim 17, further comprising determining an observed phenotype for each cell or cell population by capturing a microscopic image of the cell or cell population; and correlating the observed phenotype to the one or more detected optical barcodes.

26. The method of claim 22, further comprising generating a cDNA copy of the RNA prior to detecting the optical barcode.

27. The method of claim 26, further comprising amplifying the generated cDNA copy prior to detecting the optical barcode.

28. The method of claim 1 or claim 17, wherein detecting the optical barcode comprises detecting the nucleic acid sequence of the ordered segments in the optical barcode using an in situ sequencing method.

29. The method of claim 28, wherein the in situ sequencing method is fluorescent in situ RNA sequencing (FISSEQ) or in situ mRNA-seq.

30. The method of claim 28, wherein the in situ sequencing is FISSEQ.

31. The method of claim 1 or claim 17, wherein each nucleic acid sequence at each segment in the barcode is between approximately 100 to approximately 200 nucleotides.

32. The method of claim 1 or claim 17, wherein the barcode comprises 3 to 8 segments.

* * * * *